United States Patent
Soper et al.

(10) Patent No.: US 11,399,895 B2
(45) Date of Patent: Aug. 2, 2022

(54) SYSTEMS AND METHODS OF POSE ESTIMATION AND CALIBRATION OF PERSPECTIVE IMAGING SYSTEM IN IMAGE GUIDED SURGERY

(71) Applicant: INTUITIVE SURGICAL OPERATIONS, INC., Sunnyvale, CA (US)

(72) Inventors: Timothy D. Soper, San Jose, CA (US); Federico Barbagli, San Francisco, CA (US); Caitlin Q. Donhowe, Mountain View, CA (US); Vincent Duindam, San Francisco, CA (US); Michael D. Paris, San Francisco, CA (US); Oliver Wagner, Mountain View, CA (US); Tao Zhao, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 945 days.

(21) Appl. No.: 16/076,409

(22) PCT Filed: Feb. 10, 2017

(86) PCT No.: PCT/US2017/017391
§ 371 (c)(1),
(2) Date: Aug. 8, 2018

(87) PCT Pub. No.: WO2017/139591
PCT Pub. Date: Aug. 17, 2017

(65) Prior Publication Data
US 2019/0038365 A1 Feb. 7, 2019

Related U.S. Application Data

(60) Provisional application No. 62/294,845, filed on Feb. 12, 2016, provisional application No. 62/294,857, filed on Feb. 12, 2016.

(51) Int. Cl.
*A61B 34/20* (2016.01)
*A61B 90/00* (2016.01)
(Continued)

(52) U.S. Cl.
CPC .............. *A61B 34/20* (2016.02); *A61B 6/025* (2013.01); *A61B 6/12* (2013.01); *A61B 6/487* (2013.01);
(Continued)

(58) Field of Classification Search
CPC ......... A61B 34/20; A61B 6/547; A61B 6/582; A61B 6/025; A61B 6/12; A61B 6/487;
(Continued)

(56) References Cited

U.S. PATENT DOCUMENTS

| 6,380,732 B1 | 4/2002 | Gilboa |
| 6,389,187 B1 | 5/2002 | Greenaway et al. |

(Continued)

FOREIGN PATENT DOCUMENTS

| CN | 104427927 A | 3/2015 |
| EP | 1421913 A1 | 5/2004 |

(Continued)

OTHER PUBLICATIONS

Chintalapani, G., et al., "C-arm Distortion Correction Using Patient CT as a Fiducial," 4th IEEE International Symposium on Biomedical Imaging, Apr. 1, 2007, pp. 1180-1183.
(Continued)

*Primary Examiner* — Ashley K Buran
*Assistant Examiner* — Amy J Shafqat
(74) *Attorney, Agent, or Firm* — Haynes and Boone, LLP

(57) ABSTRACT

A method performed by a computing system comprises receiving, from a fluoroscopic imager, having a first set of parameters, first fluoroscopic image data of a first fiducial marker within a surgical coordinate space. The method
(Continued)

comprises receiving a configuration of the first fiducial marker within the surgical coordinate space. The method comprises determining a second set of parameters of the fluoroscopic imager in the surgical coordinate space based on the first fluoroscopic image data and the configuration of the first fiducial marker. In some embodiments, determining the second set of parameters comprises developing a calibrated model of the fiducial marker in the surgical coordinate space from the first fluoroscopic image data and the configuration of the first fiducial marker.

25 Claims, 14 Drawing Sheets

(51) Int. Cl.
| | | |
|---|---|---|
| *A61B 6/00* | (2006.01) | |
| *A61B 6/02* | (2006.01) | |
| *A61B 6/12* | (2006.01) | |
| *A61B 34/10* | (2016.01) | |
| *A61B 17/00* | (2006.01) | |
| *A61B 6/03* | (2006.01) | |
| *A61B 34/35* | (2016.01) | |

(52) U.S. Cl.
CPC .............. *A61B 6/547* (2013.01); *A61B 6/582* (2013.01); *A61B 34/10* (2016.02); *A61B 90/36* (2016.02); *A61B 90/39* (2016.02); *A61B 6/032* (2013.01); *A61B 6/4441* (2013.01); *A61B 34/35* (2016.02); *A61B 2017/00725* (2013.01); *A61B 2017/00809* (2013.01); *A61B 2034/105* (2016.02); *A61B 2034/107* (2016.02); *A61B 2034/207* (2016.02); *A61B 2034/2051* (2016.02); *A61B 2034/2055* (2016.02); *A61B 2034/2059* (2016.02); *A61B 2034/2061* (2016.02); *A61B 2090/363* (2016.02); *A61B 2090/367* (2016.02); *A61B 2090/376* (2016.02); *A61B 2090/3735* (2016.02); *A61B 2090/3966* (2016.02)

(58) Field of Classification Search
CPC ......... A61B 34/10; A61B 90/36; A61B 90/39; A61B 6/032; A61B 2017/00725; A61B 2090/367; A61B 6/4441; A61B 2034/105; A61B 2034/2059; A61B 2034/107; A61B 2034/207; A61B 34/35; A61B 2090/363; A61B 2090/3735; A61B 2017/00809; A61B 2090/376; A61B 2034/2051; A61B 2034/2055; A61B 2034/2061; A61B 2090/3966; A61B 2090/364; A61B 2090/3937
See application file for complete search history.

(56) References Cited

U.S. PATENT DOCUMENTS

| | | | |
|---|---|---|---|
| 6,714,810 B2 | 3/2004 | Grzeszczuk et al. | |
| 7,316,681 B2 | 1/2008 | Madhani et al. | |
| 7,772,541 B2 | 8/2010 | Froggatt et al. | |
| 8,900,131 B2 | 12/2014 | Chopra et al. | |
| 9,259,274 B2 | 2/2016 | Prisco | |
| 9,452,276 B2 | 9/2016 | Duindam et al. | |
| 9,743,892 B2 * | 8/2017 | Zheng | A61B 6/582 |
| 2005/0117708 A1 | 6/2005 | Cho et al. | |
| 2005/0281385 A1 | 12/2005 | Johnson et al. | |
| 2006/0013523 A1 | 1/2006 | Childers et al. | |
| 2010/0041985 A1 * | 2/2010 | Simon | A61B 34/20 600/426 |
| 2010/0099951 A1 | 4/2010 | Laby et al. | |
| 2010/0168562 A1 | 7/2010 | Zhao et al. | |
| 2010/0305427 A1 | 12/2010 | Huber et al. | |
| 2011/0116693 A1 | 5/2011 | Li et al. | |
| 2011/0276059 A1 | 11/2011 | Nowlin et al. | |
| 2013/0090552 A1 | 4/2013 | Ramamurthy et al. | |
| 2014/0130810 A1 | 5/2014 | Azizian et al. | |
| 2014/0275997 A1 | 9/2014 | Chopra et al. | |
| 2014/0276937 A1 | 9/2014 | Wong et al. | |
| 2015/0193946 A1 * | 7/2015 | Wong | G06T 7/248 382/103 |
| 2019/0320995 A1 * | 10/2019 | Amiri | A61B 34/00 |

FOREIGN PATENT DOCUMENTS

| | | |
|---|---|---|
| EP | 1504726 A1 | 2/2005 |
| JP | H0824248 A | 1/1996 |
| JP | 2008136866 A | 6/2008 |
| JP | 2013542768 A | 11/2013 |
| WO | WO-0187136 A2 | 11/2001 |
| WO | WO-2012158324 A2 | 11/2012 |
| WO | WO-2013016286 A2 | 1/2013 |
| WO | WO-2014150509 A1 | 9/2014 |
| WO | WO-2015010859 A1 | 1/2015 |
| WO | WO-2016018646 A1 | 2/2016 |
| WO | WO-2017030913 A2 | 2/2017 |
| WO | WO-2017030915 A1 | 2/2017 |

OTHER PUBLICATIONS

Extended European Search Report for Application No. EP17750840.5 dated Sep. 5, 2019, 14 pages.
Yao, Jianhua et al., "A C-arm fluoroscopy-guided progressive cut refinement strategy using a surgical robot," Computer Aided Surgery, 2000, pp. 373-390, vol. 5-No. 6, Wiley-Liss, Inc.
International Preliminary Report on Patentability for Application No. PCT/US2017/017391, dated Aug. 14, 2018, 15 pages.
International Search Report and Written Opinion for Application No. PCT/US2017/017391, dated Jun. 15, 2017, 17 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

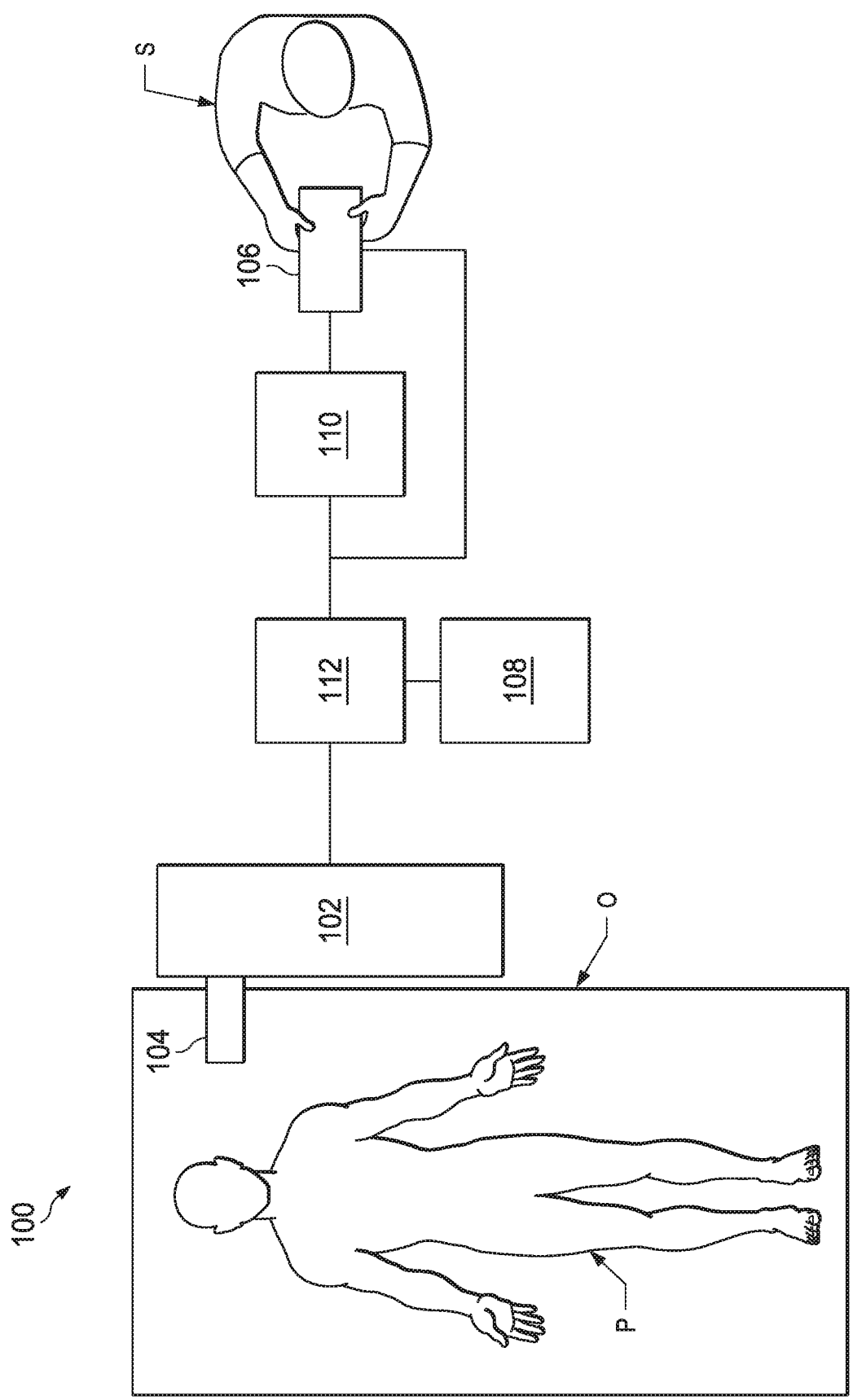

SYSTEMS AND METHODS OF POSE ESTIMATION AND CALIBRATION OF PERSPECTIVE IMAGING SYSTEM IN IMAGE GUIDED SURGERY

This patent application is the U.S. national phase of International Application No. PCT/US17/17391, filed Feb. 10, 2017, which designated the U.S. and claims priority to and the benefit of the filing date of U.S. Provisional Patent Application No. 62/294,845, entitled "SYSTEMS AND METHODS OF POSE ESTIMATION AND CALIBRATION OF PERSPECTIVE IMAGING SYSTEM IN IMAGE GUIDED SURGERY," filed Feb. 12, 2016, and U.S. Provisional Patent Application No. 62/294,857 entitled "SYSTEMS AND METHODS OF POSE ESTIMATION AND CALIBRATION OF PERSPECTIVE IMAGING SYSTEM IN IMAGE GUIDED SURGERY," filed Feb. 12, 2016, both of which are hereby, incorporated by reference in their entirety.

FIELD

The present disclosure is directed to systems and methods for conducting an image guided procedure, and more particularly to systems and methods for pose estimation, calibration of a perspective imaging system, and real-time tomosynthesis to enhance the accuracy of tool navigation during an image guided procedure.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions clinicians may insert minimally invasive medical instruments (including surgical, diagnostic, therapeutic, or biopsy instruments) to reach a target tissue location. To assist with reaching the target tissue location, the location and movement of the medical instruments may be registered with pre-operative or intra-operative images of the patient anatomy. With the image-guided instruments registered to the images, the instruments may navigate natural or surgically created passageways in anatomical systems such as the lungs, the colon, the intestines, the kidneys, the heart, the circulatory system, or the like. Some image-guided instruments may include a fiber-optic shape sensor which provides information about the shape of an elongated flexible instrument and about the pose of the instrument's distal end. In some embodiments, perspective imaging systems are used intra-operatively to assist in localizing targets and/or the instruments during the procedure. In order for the imaging data to assist in correctly localizing the medical instrument, the imaging system must be accurately registered to the coordinate system of the surgical environment. Systems and techniques for minimizing errors associated with pose estimation and calibration of the imaging system to the surgical environment are needed to more reliably localize and navigate medical instruments within the surgical environment.

SUMMARY

The embodiments of the invention are summarized by the claims that follow the description.

In one embodiment, a method performed by a computing system comprises receiving, from a fluoroscopic imager having a first set of parameters, first fluoroscopic image data of a first fiducial marker within a surgical coordinate space. The method also comprises receiving a configuration of the first fiducial marker within the surgical coordinate space. The method also comprises determining a second set of parameters of the fluoroscopic imager in the surgical coordinate space based on the first flouroscopic image data and the configuration of the first fiducial marker. In one aspect, determining the second set of parameters comprises developing a calibrated model of the fiducial marker in the surgical coordinate space from the first fluoroscopic image data and the configuration of the first fiducial marker.

In another embodiment, a computer-assisted medical system comprises one or more processors and a first fiducial marker positioned in a known configuration within a surgical coordinate space. The first fiducial marker includes a shape sensor. The one or more processors perform a method including receiving, from a fluoroscopic imager, first fluoroscopic image data of the first fiducial marker positioned in the known configuration within the surgical coordinate space and receiving shape information from the shape sensor. The method also includes determining the known configuration of the first fiducial marker within the surgical coordinate space from the shape information and determining from the first fluoroscopic image data a calibrated model of the fiducial marker in the surgical coordinate space. The method further includes determining a pose of the fluoroscopic imager in the surgical coordinate space based on the first fluoroscopic image data.

In another embodiment, a computer-assisted medical system comprises a fluoroscopic imager having a full scan range of a surgical coordinate space, and one or more processors, wherein the one or more processors are configured to perform a method. In one aspect, the method comprises receiving a first fluoroscopic image data set of a patient anatomy from the fluoroscopic imager and receiving at least one additional fluoroscopic image data set of the patient anatomy from the fluoroscopic imager operating in a constrained range substantially smaller than the full scan range. The method also comprises constructing a first planar tomographic image from the first and at least one additional fluoroscopic image data sets.

In another embodiment, a method of localized tomosynthesis comprises receiving a first fluoroscopic image data set of a patient anatomy, the first fluoroscopic image data set obtained from a full scan range of a fluoroscopic imager. The method also comprises receiving at least one additional fluoroscopic image data set of the patient anatomy from the fluoroscopic imager operating in a constrained range substantially smaller than the full scan range. The method also comprises constructing a first planar tomographic image from the first and at least one additional fluoroscopic image data sets. In one aspect, the method also comprises, based on the first planar tomographic image, operating the fluoroscopic imager in a second constrained region substantially smaller than the full scan range. In one aspect, the method also comprises constructing a second planar tomographic image from a fluoroscopic image data set received while the fluoroscopic imager is in the second constrained region.

In another embodiment, a method of localized tomosynthesis comprises moving a fluoroscopic imager to a first position in a constrained range, wherein the fluoroscopic imager has a full scan range and wherein the constrained range is substantially smaller than the full scan range. The method also comprises obtaining a first fluoroscopic image of a patient anatomy from the first position, moving the fluoroscopic imager to a plurality of additional positions within the constrained range, obtaining a fluoroscopic image from each of the plurality of additional positions, and constructing a first planar tomographic image from the first fluoroscopic image and the fluoroscopic images obtained from each of the plurality of additional positions.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 1 is a teleoperated medical system, in accordance with embodiments of the present disclosure.

Figure 7A:
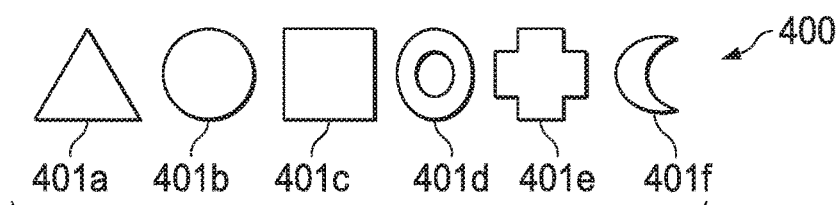
Figure 7B:
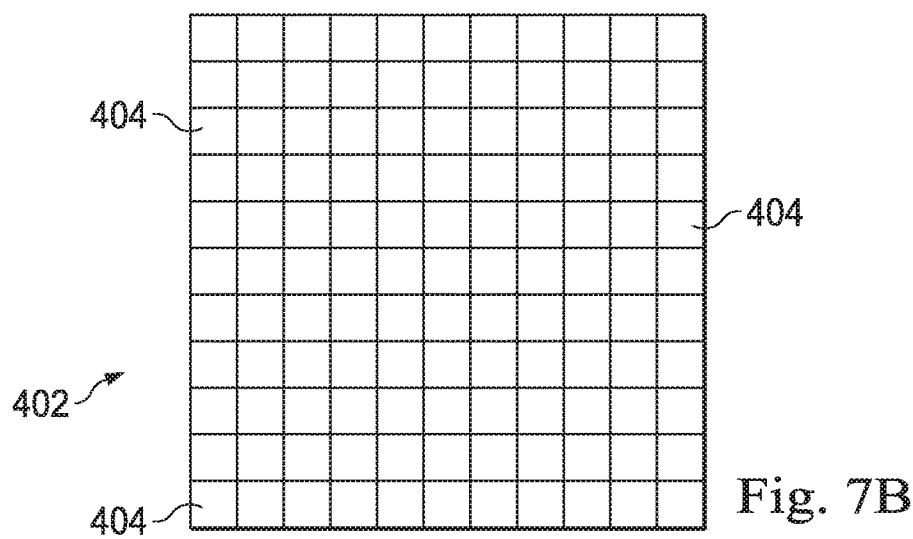
Figure 7C:
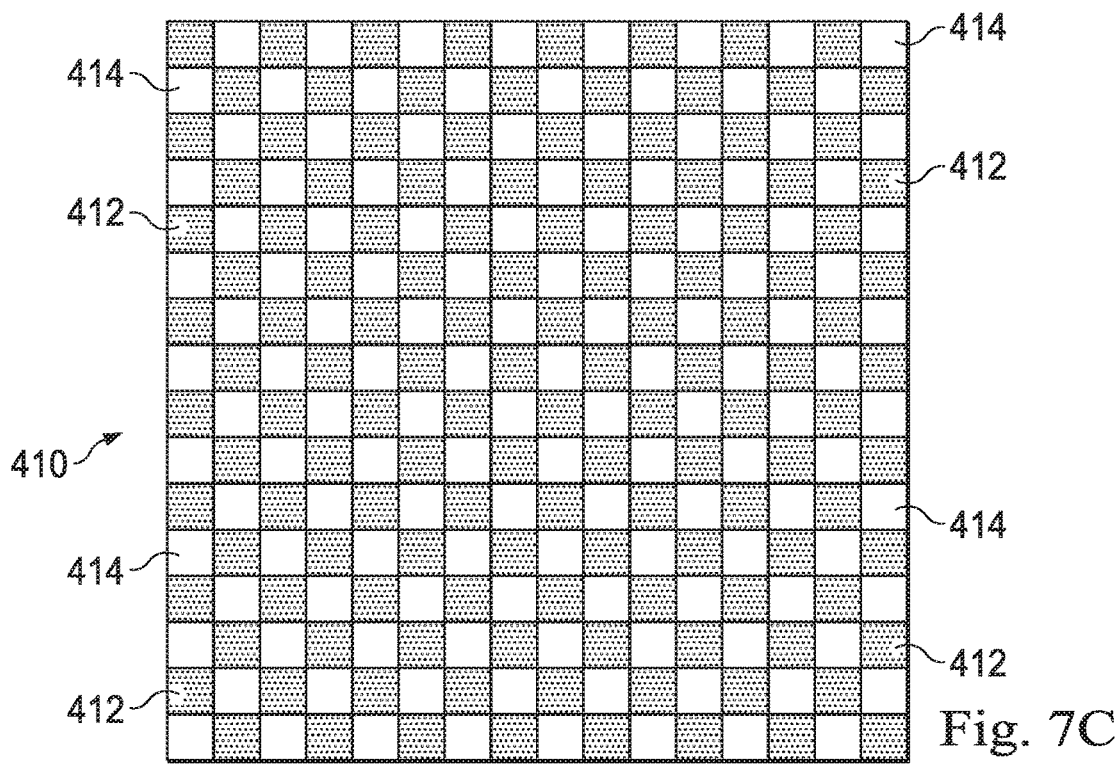
Figure 8A:
Figure 8B:
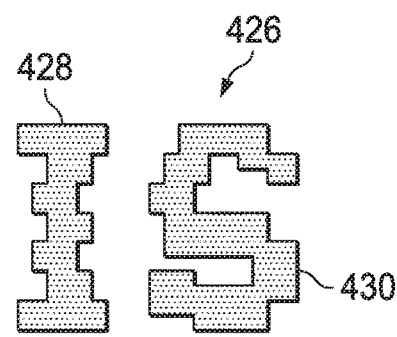
Figure 8C:
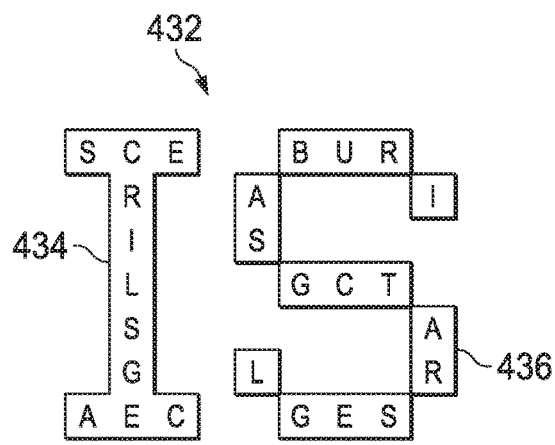
Figure 8D:
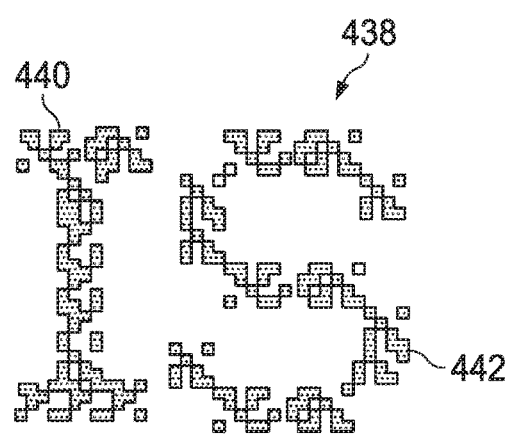
Figure 8E:
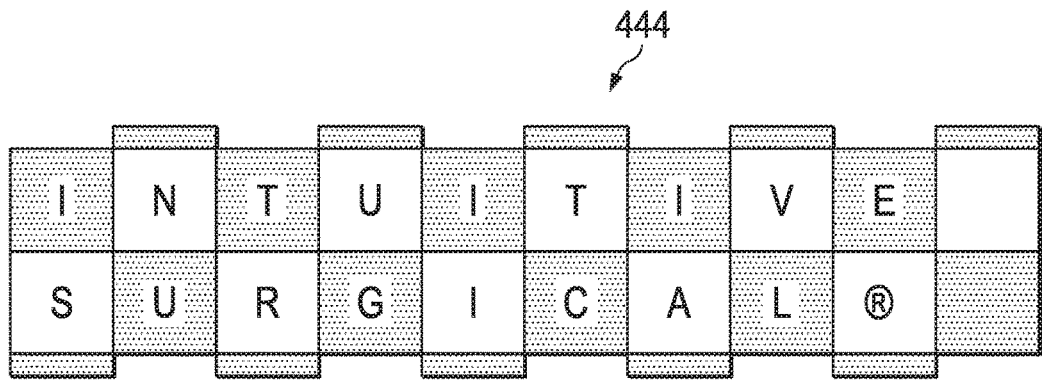

FIGS. 7A-7C illustrate a variety of exemplary fiducial markers according to various embodiments of the present disclosure. FIG. 7A illustrates an exemplary fiducial marker comprising a set of distinctive marker elements. FIG. 7B illustrates a fiducial marker comprising a grid pattern. FIG. 7C illustrates a fiducial marker comprising a checkerboard pattern.

FIGS. 8A-8E illustrate several exemplary discernible fiducial markers according to various embodiments of the present disclosure.

Figure 9A:
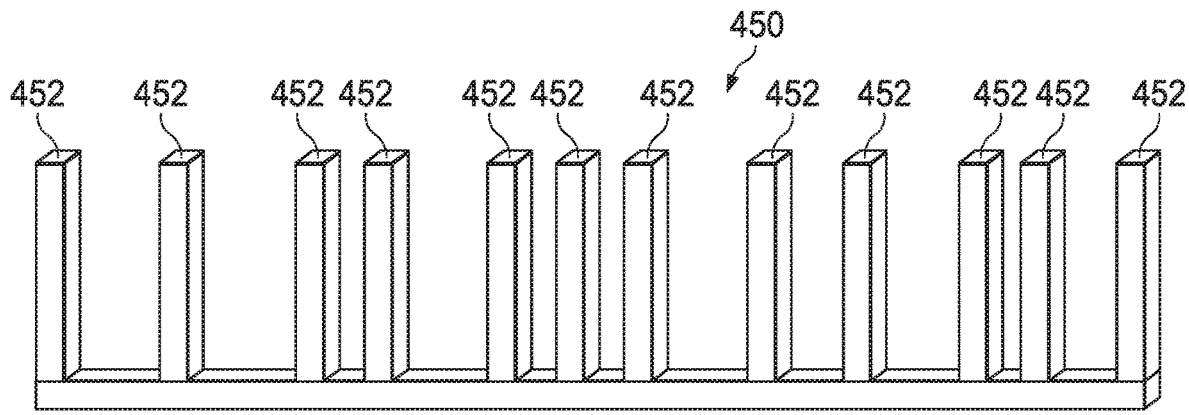
Figure 9B:
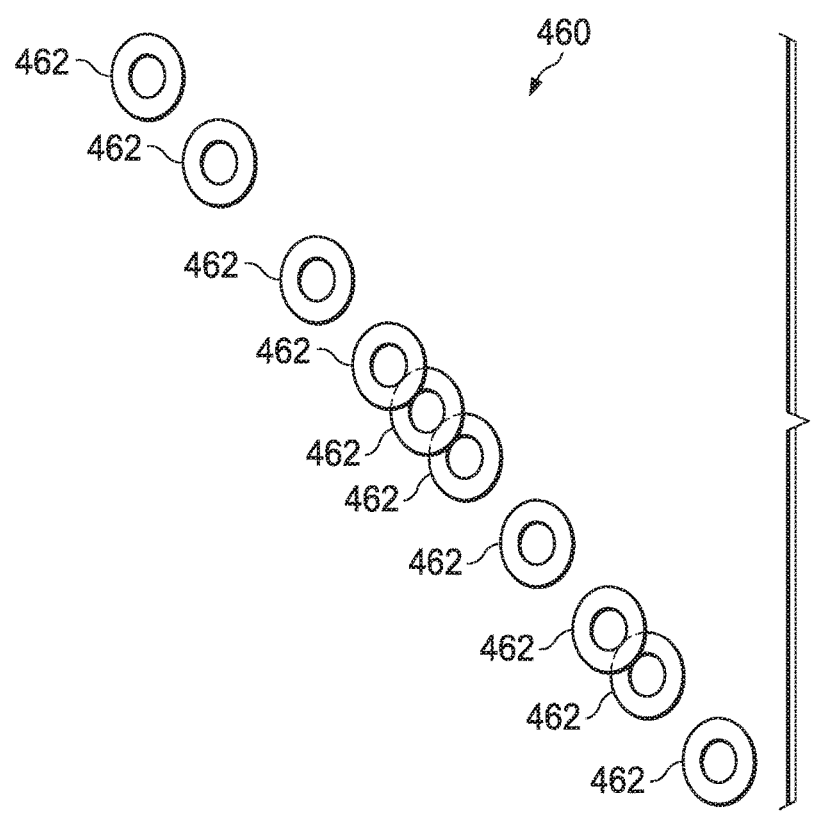

FIGS. 9A and 9B illustrate fiducial markers having marker elements arranged in a non-uniform linear pattern according to embodiments of the present disclosure.

Figure 10:
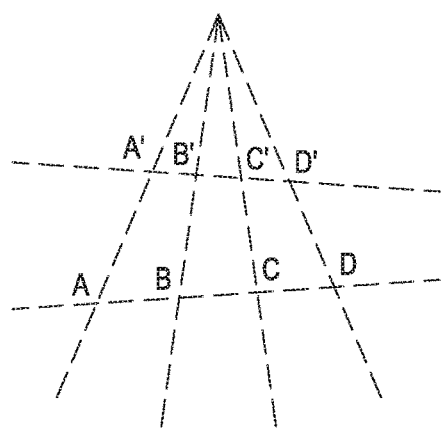

FIG. 10 is a diagram illustrating the cross-ratio and projective invariance principle.

Figure 11:
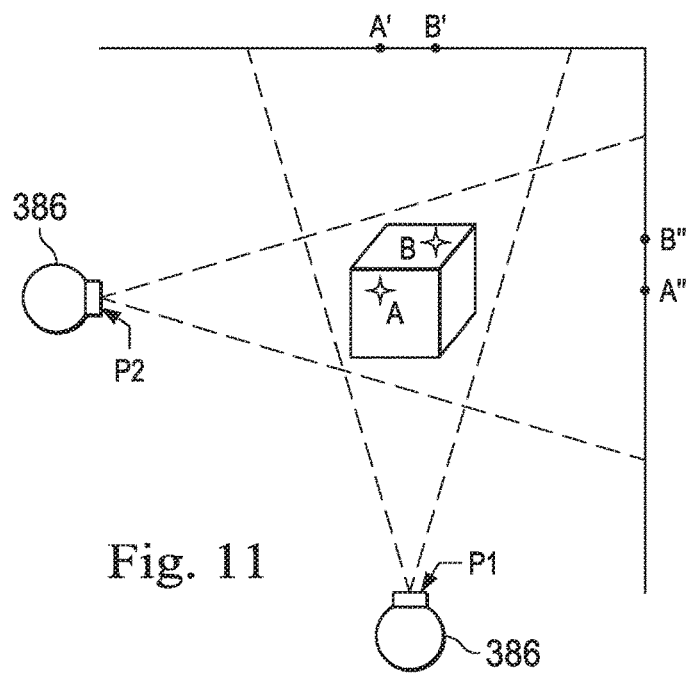

FIG. 11 is a diagram illustrating the principle of projective invariance in an image-guided surgical procedure in which the perspective imager images a stationary fiducial marker from two different positions.

Figure 12:
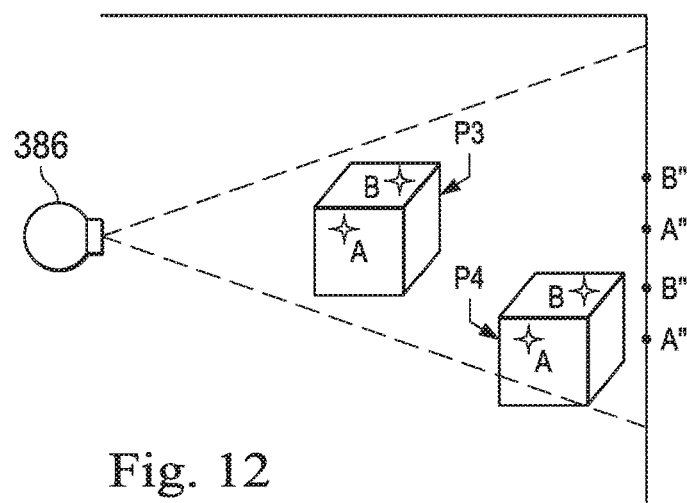

FIG. 12 is a diagram illustrating the principle of projective invariance in an image-guided surgical procedure in which a stationary perspective imager images a fiducial marker placed in two different positions.

Figure 13:
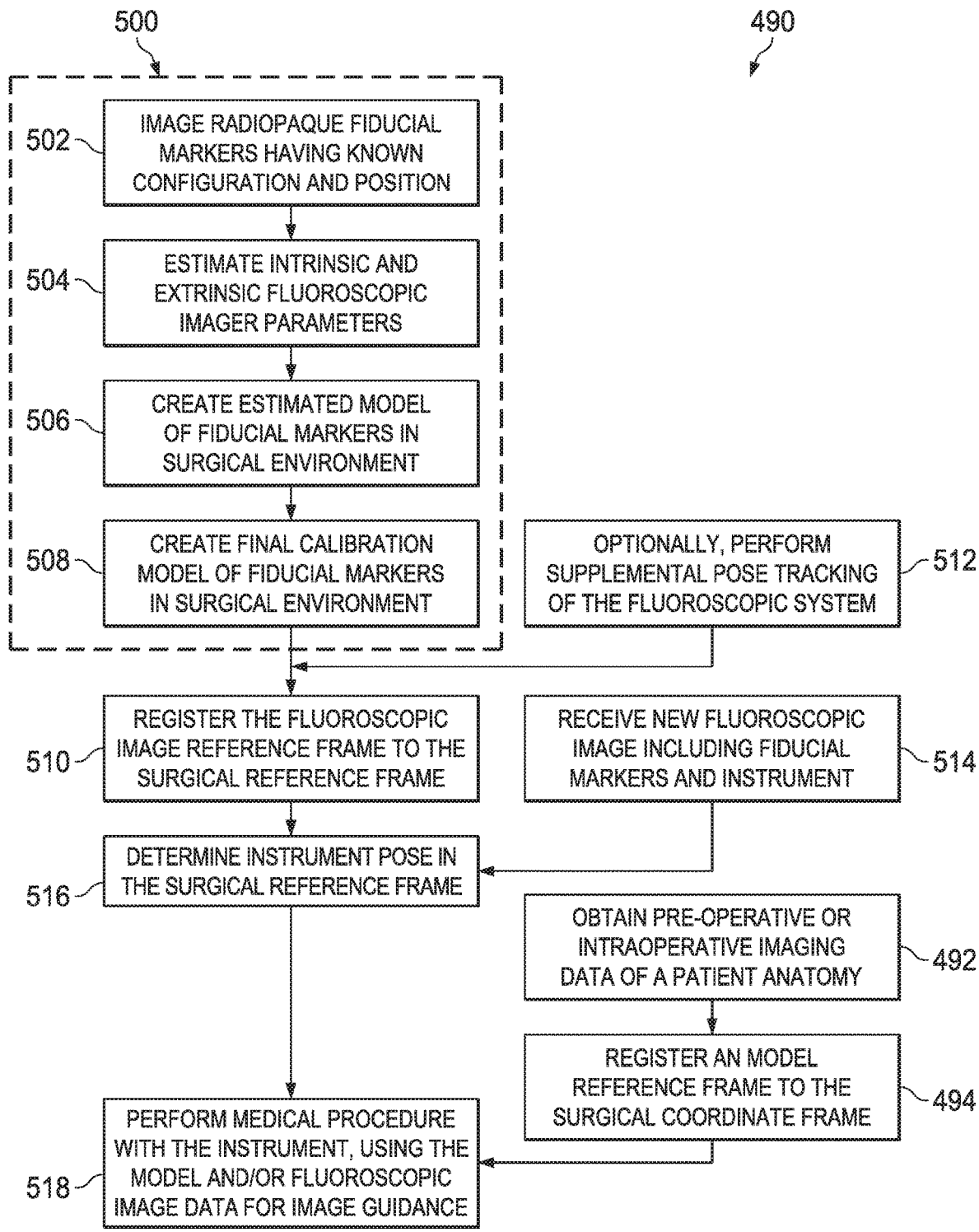

FIG. 13 illustrates a flowchart of a portion of an image-guided medical procedure according to an embodiment of the present disclosure.

Figure 14:
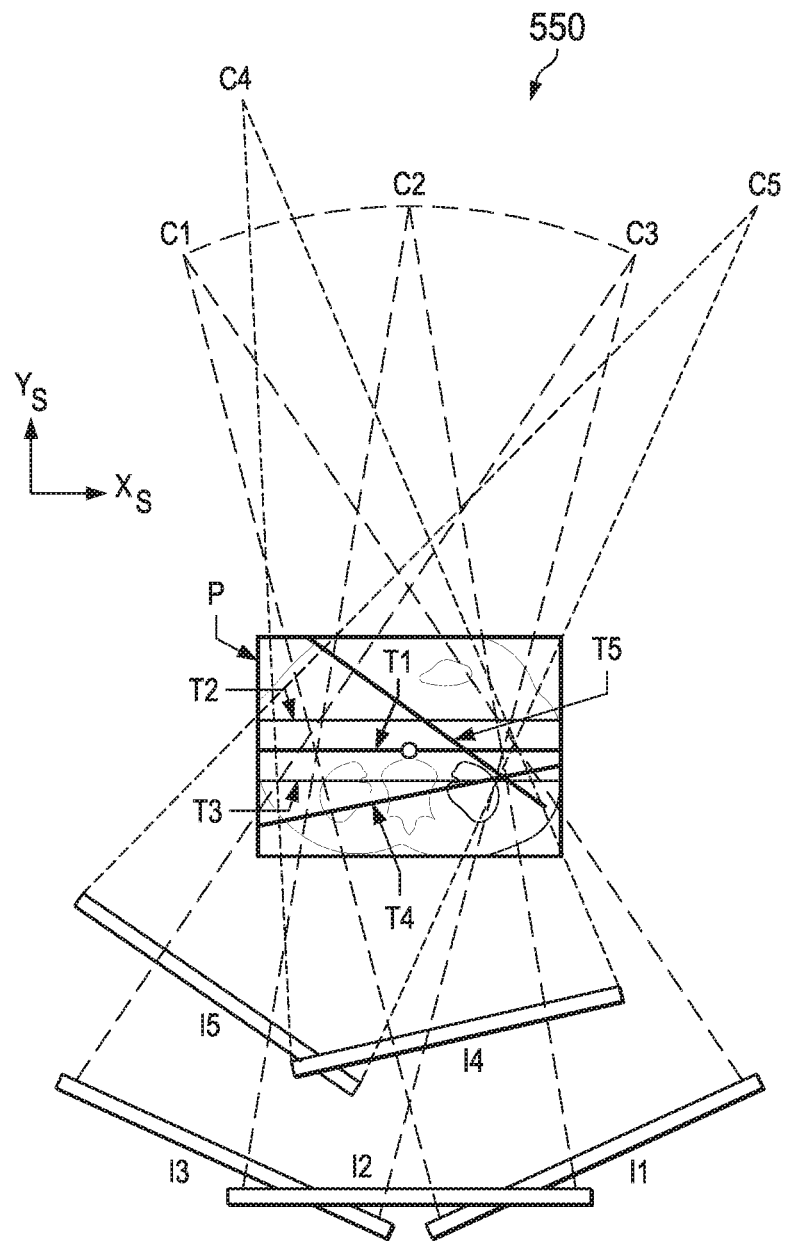

FIG. 14 illustrates a patient anatomy and a tomosynthesis arrangement in as viewed from a plane of a surgical environment.

Figure 15:
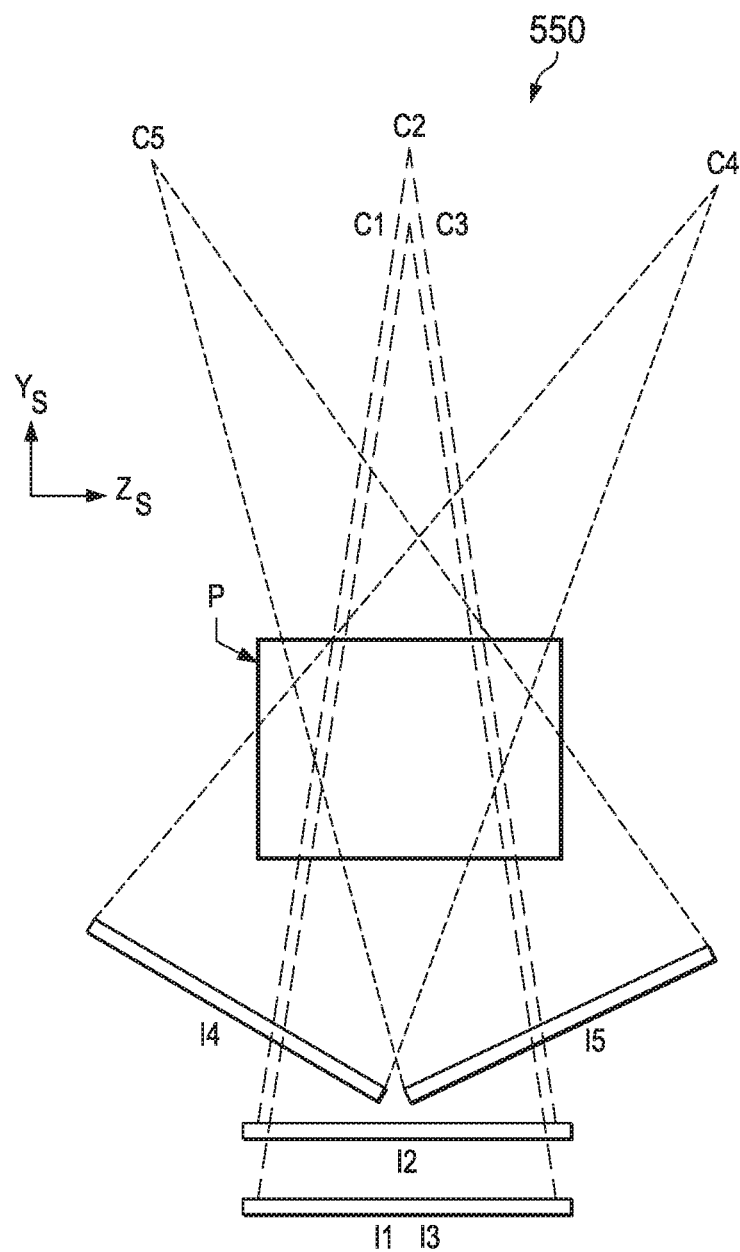

FIG. 15 illustrates the patient anatomy and tomosynthesis arrangement of FIG. 14 as viewed from an orthogonal plane.

Figure 16:
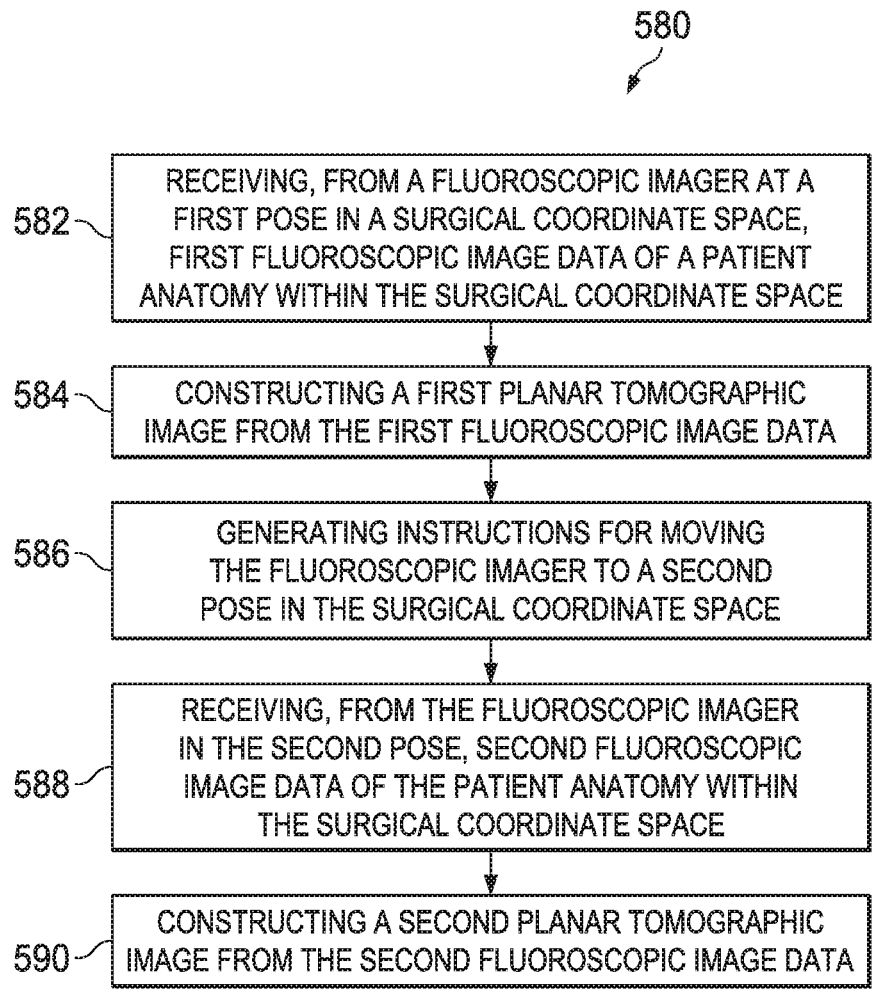

FIG. 16 illustrates a flowchart of an image guided medical procedure according to an embodiment of the present disclosure.

DETAILED DESCRIPTION

In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention. And, to avoid needless descriptive repetition, one or more components or actions described in accordance with one illustrative embodiment can be used or omitted as applicable from other illustrative embodiments.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Referring to FIG. 1 of the drawings, a teleoperated medical system for use in, for example, surgical, diagnostic, therapeutic, or biopsy procedures, is generally indicated as a teleoperated medical system 100. As shown in FIG. 1, the teleoperated system 100 generally includes a teleoperational manipulator assembly 102 for operating a medical instrument system 104 in performing various procedures on the patient P. The teleoperational manipulator assembly 102 is also referred to as the "teleoperational assembly 102" or the "manipulator assembly 102." The medical instrument system 104 is also referred to as the "medical instrument 104."

The assembly 102 is mounted to or near an operating table O. An operator input system 106 (also called the "master assembly 106") allows the clinician or surgeon S to view the interventional site and to control the manipulator assembly 102.

The operator input system 106 may be located at a surgeon's console which is usually located in the same room as operating table O. However, it should be understood that the surgeon S can be located in a different room or a completely different building from the patient P. The operator input assembly 106 generally includes one or more control devices for controlling the manipulator assemblies 102. The control devices may include any number of a variety of input devices, such as joysticks, trackballs, data gloves, trigger-guns, hand-operated controllers, voice recognition devices, body motion or presence sensors, or the like. In some embodiments, the control devices will be provided with the same degrees of freedom as the associated medical instruments 104 to provide the surgeon with telepresence, or the perception that the control devices are integral with the instruments 104 so that the surgeon has a strong sense of directly controlling instruments 104. In other embodiments, the control devices may have more or fewer degrees of freedom than the associated medical instruments 104 and still provide the surgeon with telepresence. In some embodiments, the control devices are manual input devices which move with six degrees of freedom, and which may also include an actuatable handle for actuating instruments (for example, for closing grasping jaws, applying an electrical potential to an electrode, delivering a medicinal treatment, or the like).

The teleoperational assembly 102 supports the medical instrument system 104 and may include a kinematic structure of one or more non-servo controlled links (e.g., one or more links that may be manually positioned and locked in place, generally referred to as a set-up structure) and a teleoperational manipulator. The teleoperational assembly 102 includes plurality of actuators or motors that drive inputs on the medical instrument system 104 in response to commands from the control system (e.g., a control system 112). The motors include drive systems that when coupled to the medical instrument system 104 may advance the medical instrument into a naturally or surgically created anatomic orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like. Motor position sensors such as resolvers, encoders, potentiometers, and other mechanisms may provide sensor data to the teleoperational assembly describing the rotation and orientation of the motor shafts. This position sensor data may be used to determine motion of the objects manipulated by the motors.

The teleoperational medical system 100 also includes a sensor system 108 with one or more sub-systems for receiving information about the instruments of the teleoperational assembly. Such sub-systems may include a position/location sensor system (e.g., an electromagnetic (EM) sensor system); a shape sensor system for determining the position, orientation, speed, velocity, pose, and/or shape of the catheter tip and/or of one or more segments along a flexible body of instrument system 104; and/or a visualization system for capturing images from the distal end of the catheter system.

The visualization system (e.g., visualization system 231 of FIG. 2A) may include a viewing scope assembly that records a concurrent or real-time image of the surgical site and provides the image to the clinician or surgeon S. The concurrent image may be, for example, a two or three dimensional image captured by a perspective imaging system positioned outside the surgical site. In some embodiments, the perspective imaging system includes an imager that creates two dimensional images, such as, by way of non-limiting example, a fluoroscopic or X-ray imager or an optical camera. Additionally or alternatively, the concurrent image may be, for example, a two or three dimensional image captured by an endoscope positioned within the surgical site. In this embodiment, the visualization system includes endoscopic components that may be integrally or removably coupled to the medical instrument 104. In alternative embodiments, however, a separate endoscope attached to a separate manipulator assembly may be used with the medical instrument to image the surgical site. The visualization system may be implemented as hardware, firmware, software or a combination thereof which interact with or are otherwise executed by one or more computer processors, which may include the processors of a control system 112 (described below). The processors of the control system 112 may execute instructions comprising instruction corresponding to processes disclosed herein.

The teleoperational medical system 100 also includes a display system 110 for displaying an image or representation of the surgical site and medical instrument system(s) 104 generated by sub-systems of the sensor system 108. The display system 110 and the operator input system 106 may be oriented so the operator can control the medical instrument system 104 and the operator input system 106 with the perception of telepresence.

The display system 110 may also display an image of the surgical site and medical instruments captured by the visualization system. The display system 110 and the control devices may be oriented such that the relative positions of the imaging device in the scope assembly and the medical instruments are similar to the relative positions of the surgeon's eyes and hands so the operator can manipulate the medical instrument 104 and the hand control as if viewing the workspace in substantially true presence. By true presence, it is meant that the presentation of an image is a true perspective image simulating the viewpoint of an operator that is physically manipulating the instrument 104.

Alternatively or additionally, the display system 110 may present images of the surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, or nanotube X-ray imaging. The pre-operative or intra-operative image data may be presented as two-dimensional, three-dimensional, or four-dimensional (including e.g., time based or velocity based information) images or as images from models created from the pre-operative or intra-operative image data sets.

In some embodiments often for purposes of imaged guided surgical procedures, the display system 110 may display a virtual navigational image in which the actual location of the medical instrument 104 is registered (i.e., dynamically referenced) with the preoperative or concurrent images/model to present the clinician or surgeon S with a virtual image of the internal surgical site from the viewpoint of the location of the tip of the instrument 104. An image of the tip of the instrument 104 or other graphical or alphanumeric indicators may be superimposed on the virtual image to assist the surgeon controlling the medical instrument. Alternatively, the instrument 104 may not be visible in the virtual image.

In other embodiments, the display system 110 may display a virtual navigational image in which the actual location of the medical instrument is registered with preoperative or concurrent images to present the clinician or surgeon S with a virtual image of medical instrument within the surgical site from an external viewpoint. An image of a portion of the medical instrument or other graphical or alphanumeric indicators may be superimposed on the virtual image to assist the surgeon controlling the instrument 104.

The teleoperational medical system 100 also includes a control system 112. The control system 112 includes at least one memory and at least one computer processor (not shown), and typically a plurality of processors, for effecting control between the medical instrument system 104, the operator input system 106, the sensor system 108, and the display system 110. The control system 112 also includes programmed instructions (e.g., a computer-readable medium storing the instructions) to implement some or all of the methods described in accordance with aspects disclosed herein, including instructions for providing pathological information to the display system 110. While control system 112 is shown as a single block in the simplified schematic of FIG. 1, the system may include two or more data processing circuits with one portion of the processing optionally being performed on or adjacent the teleoperational assembly 102, another portion of the processing being performed at the operator input system 106, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may include one or more servo controllers that receive force and/or torque feedback from the medical instrument system 104. Responsive to the feedback, the servo controllers transmit signals to the operator input system 106. The servo controller(s) may also transmit signals instructing teleoperational assembly 102 to move the medical instrument system(s) 104 which extend into an internal surgical site within the patient body via openings in the body. Any suitable conventional or specialized servo controller may be used. A servo controller may be separate from, or integrated with, teleoperational assembly 102. In some embodiments, the servo controller and teleoperational assembly are provided as part of a teleoperational arm cart positioned adjacent to the patient's body.

The control system 112 may further include a virtual visualization system to provide navigation assistance to the medical instrument system(s) 104 when used in an image-guided surgical procedure. Virtual navigation using the virtual visualization system is based upon reference to the acquired preoperative or intraoperative dataset of the anatomic passageways. More specifically, the virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software alone or in combination with manual input is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intraoperatively during a clinical procedure. In an alternative embodiment, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, the sensor system 108 may be used to compute an approximate location of the instrument with respect to the patient anatomy. The location can be used to produce both macro-level (external) tracking images of the patient anatomy and virtual internal images of the patient anatomy. Various systems for using electromagnetic (EM) sensor, fiber optic sensors, or other sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such system.

The teleoperational medical system 100 may further include optional operation and support systems (not shown) such as illumination systems, steering control systems, irrigation systems, and/or suction systems. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated or they may be positioned in separate locations. Multiple operator input systems allow more than one operator to control one or more manipulator assemblies in various combinations.

Figure 2A:
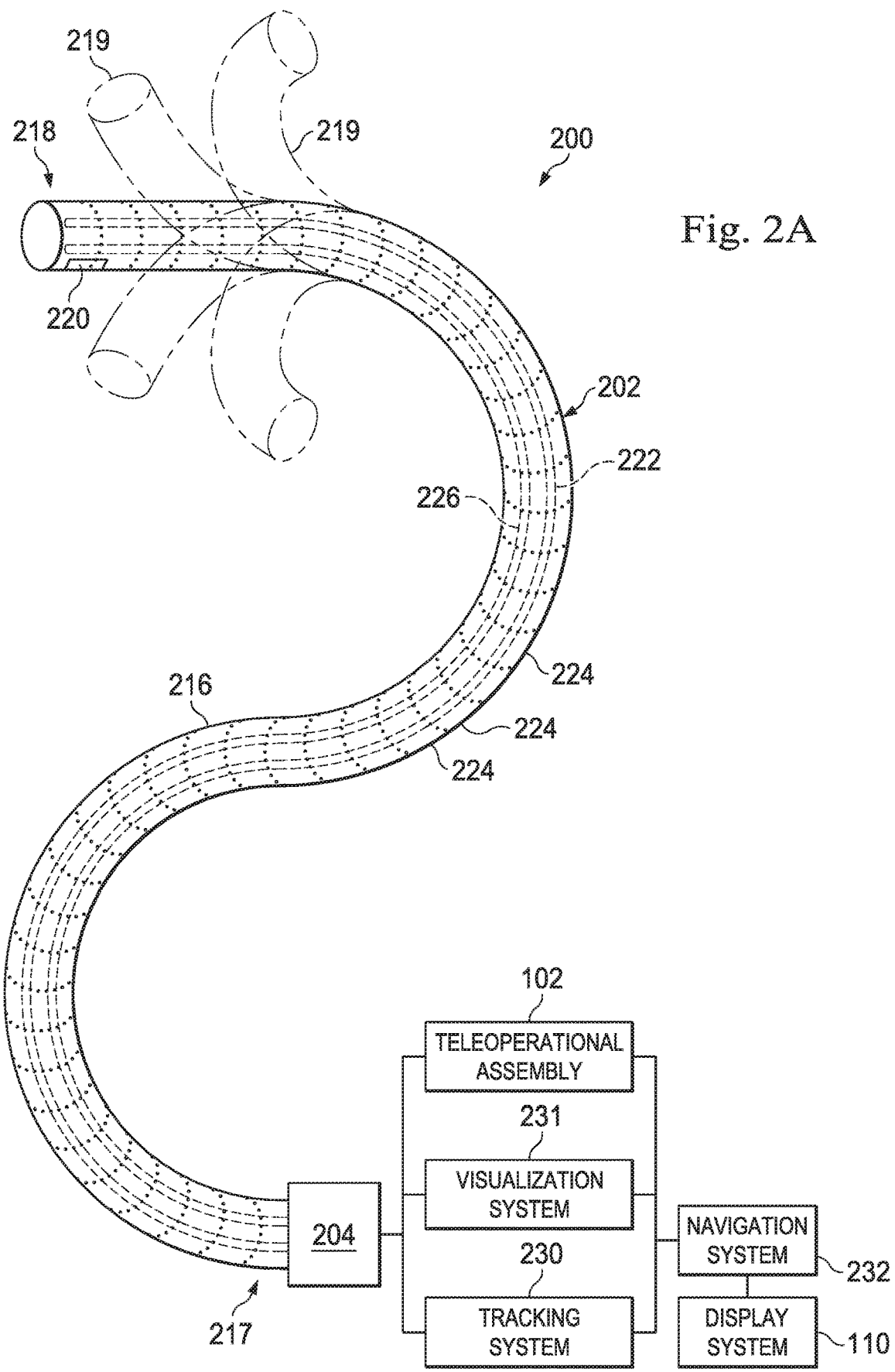
FIG. 2A illustrates a medical instrument system utilizing aspects of the present disclosure.

FIG. 2A illustrates a medical instrument system 200, which may be used as the medical instrument system 104 in an image-guided medical procedure performed with teleoperational medical system 100. Alternatively, the medical instrument system 200 may be used for non-teleoperational exploratory procedures or in procedures involving traditional manually operated medical instruments, such as endoscopy. Additionally or alternatively the medical instrument system 200 may be used to gather (i.e., measure) a set of data points corresponding to locations with patient anatomic passageways.

The instrument system 200 includes a catheter system 202 coupled to an instrument housing 204. The catheter system 202 includes an elongated flexible catheter body 216 having a proximal end 217 and a distal end 218 (also called "tip portion 218"). In one embodiment, the flexible body 216 has an approximately 3 mm outer diameter. Other flexible body outer diameters may be larger or smaller. The catheter system 202 may optionally include a shape sensor system 222 (also called "shape sensor 222") for determining the position, orientation, speed, velocity, pose, and/or shape of the catheter tip at distal end 218 and/or of one or more segments 224 along the body 216. The entire length of the body 216, between the distal end 218 and the proximal end 217, may be effectively divided into the segments 224. If the instrument system 200 is a medical instrument system 104 of a teleoperational medical system 100, the shape sensor 222 may be a component of the sensor system 108. If the instrument system 200 is manually operated or otherwise used for non-teleoperational procedures, the shape sensor 222 may be coupled to a tracking system 230 that interrogates the shape sensor and processes the received shape data.

The shape sensor 222 may include an optical fiber aligned with the flexible catheter body 216 (e.g., provided within an interior channel (not shown) or mounted externally). In one embodiment, the optical fiber has a diameter of approximately 200 µm. In other embodiments, the dimensions may be larger or smaller. The optical fiber of the shape sensor system 222 forms a fiber optic bend sensor for determining the shape of the catheter system 202. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in alternative embodiments may employ other suitable strain sensing techniques, such as Rayleigh scattering, Raman scattering, Brillouin scattering, and Fluorescence scattering. In other alternative embodiments, the shape of the catheter may be determined using other techniques. For example, the history of the catheter's distal tip pose can be used to reconstruct the shape of the device over the interval of time. As another example, historical pose, position, or orientation data may be stored for a known point of an instrument system along a cycle of alternating motion, such as breathing. This stored data may be used to develop shape information about the catheter. Alternatively, a series of positional sensors, such as electromagnetic (EM) sensors, positioned along the catheter can be used for shape sensing. Alternatively, a history of data from a positional sensor, such as an EM sensor, on the instrument system during a procedure may be used to represent the shape of the instrument, particularly if an anatomic passageway is generally static. Alternatively, a wireless device with position or orientation controlled by an external magnetic field may be used for shape sensing. The history of the wireless device's position may be used to determine a shape for the navigated passageways.

The medical instrument system may, optionally, include a position sensor system 220. The position sensor system 220 may be a component of an EM sensor system with the sensor system 220 including one or more conductive coils that may be subjected to an externally generated electromagnetic field. In such an embodiment, each coil of the EM sensor system comprising the position sensor system 220 then produces an induced electrical signal having characteristics that depend on the position and orientation of the coil relative to the externally generated electromagnetic field. In one embodiment, the EM sensor system may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of an EM sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety. In some embodiments, the shape sensor may also function as the position sensor because the shape of the sensor together with information about the location of the base of the shape sensor (in the fixed coordinate system of the patient) allows the location of various points along the shape sensor, including the distal tip, to be calculated.

A tracking system 230 may include the position sensor system 220 and a shape sensor system 222 for determining the position, orientation, speed, pose, and/or shape of the distal end 218 and of one or more segments 224 along the instrument system 200. The tracking system 230 may be implemented as hardware, firmware, software or a combination thereof which interact with or are otherwise executed by one or more computer processors, which may include the processors of a control system 116.

The flexible catheter body 216 includes a channel 221 sized and shaped to receive a medical instrument 226. Medical instruments may include, for example, image capture probes, biopsy instruments, laser ablation fibers, or other surgical, diagnostic, or therapeutic tools. Medical tools may include end effectors having a single working member such as a scalpel, a blunt blade, an optical fiber, or an electrode. Other end effectors may include, for example, forceps, graspers, scissors, or clip appliers. Examples of electrically activated end effectors include electrosurgical electrodes, transducers, sensors, and the like. In various embodiments, the medical instrument 226 may be an image capture probe that includes a distal portion with a stereoscopic or monoscopic camera at or near the distal end 218 of the flexible catheter body 216 for capturing images (including video images) that are processed by a visualization system 231 for display. The image capture probe may include a cable coupled to the camera for transmitting the captured image data. Alternatively, the image capture instrument may be a fiber-optic bundle, such as a fiberscope, that couples to the visualization system. The image capture instrument may be single or multi-spectral, for example capturing image data in one or more of the visible, infrared, or ultraviolet spectrums.

The medical instrument 226 may house cables, linkages, or other actuation controls (not shown) that extend between the proximal and distal ends of the instrument to controllably bend the distal end of the instrument. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

The flexible catheter body 216 may also houses cables, linkages, or other steering controls (not shown) that extend between the housing 204 and the distal end 218 to controllably bend the distal end 218 as shown, for example, by the broken dashed line depictions 219 of the distal end. Steerable catheters are described in detail in U.S. patent application Ser. No. 13/274,208 (filed Oct. 14, 2011) (disclosing "Catheter with Removable Vision Probe"), which is incorporated by reference herein in its entirety. In embodiments in which the instrument system 200 is actuated by a teleoperational assembly, the housing 204 may include drive inputs that removably couple to and receive power from motorized drive elements of the teleoperational assembly. In embodiments in which the instrument system 200 is manually operated, the housing 204 may include gripping features, manual actuators, or other components for manually controlling the motion of the instrument system. The catheter system may be steerable or, alternatively, the system may be non-steerable with no integrated mechanism for operator control of the instrument bending. Also or alternatively, one or more lumens, through which medical instruments can be deployed and used at a target surgical location, are defined in the walls of the flexible body 216.

In various embodiments, the medical instrument system 200 may include a flexible bronchial instrument, such as a bronchoscope or bronchial catheter, for use in examination, diagnosis, biopsy, or treatment of a lung. The system 200 is also suited for navigation and treatment of other tissues, via natural or surgically created connected passageways, in any of a variety of anatomic systems, including the colon, the intestines, the kidneys, the brain, the heart, the circulatory system, and the like.

The information from the tracking system 230 may be sent to a navigation system 232 where it is combined with information from the visualization system 231 and/or the preoperatively obtained models to provide the surgeon or other operator with real-time position information on the display system 110 for use in the control of the instrument system 200. The control system 116 may utilize the position information as feedback for positioning the instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

Fiber optic shape sensors are particularly useful as localization sensors because they provide data about the entire shape of the instrument, including the pose of the distal tip, without being sensitive to metal objects in the area or requiring obstructive imaging equipment. When using fiber optic shape sensors, however, small position and orientation errors at the proximal end of the optical fiber may generate large accumulated position and orientation errors for the distal end of the sensor due to the length of the sensor (e.g., approximately one meter). Systems and methods to reduce these errors are described below and may be used to generate more accurate registrations of the optical fiber and, consequently, the medical instrument to the surgical coordinate system and to the anatomic model during the procedure.

In the embodiment of FIG. 2A, the instrument system 200 is teleoperated within the teleoperational medical system 100. In an alternative embodiment, the teleoperational assembly 102 may be replaced by direct operator control. In the direct operation alternative, various handles and operator interfaces may be included for hand-held operation of the instrument.

In alternative embodiments, the teleoperated system may include more than one slave manipulator assembly and/or more than one master assembly. The exact number of manipulator assemblies will depend on the medical procedure and the space constraints within the operating room, among other factors. The master assemblies may be collocated, or they may be positioned in separate locations. Multiple master assemblies allow more than one operator to control one or more slave manipulator assemblies in various combinations.

Figure 2B:
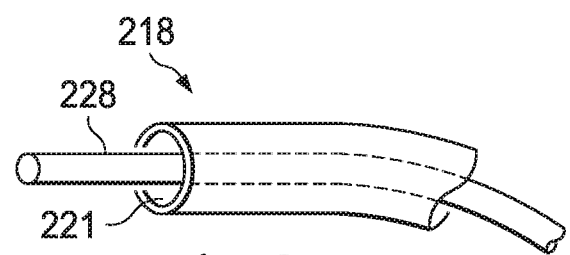
FIG. 2B illustrates a distal end of the medical instrument system of FIG. 2A with an extended medical tool, in accordance with embodiments of the present disclosure.

As shown in greater detail in FIG. 2B, medical tool(s) 228 for such procedures as surgery, biopsy, ablation, illumination, irrigation, or suction can be deployed through the channel 221 of the flexible body 216 and used at a target location within the anatomy. If, for example, the tool 228 is a biopsy instrument, it may be used to remove sample tissue or a sampling of cells from a target anatomic location. The medical tool 228 may be used with an image capture probe also within the flexible body 216. Alternatively, the tool 228 may itself be the image capture probe. The tool 228 may be advanced from the opening of the channel 221 to perform the procedure and then retracted back into the channel when the procedure is complete. The medical tool 228 may be removed from the proximal end 217 of the catheter flexible body or from another optional instrument port (not shown) along the flexible body.

Figure 3:
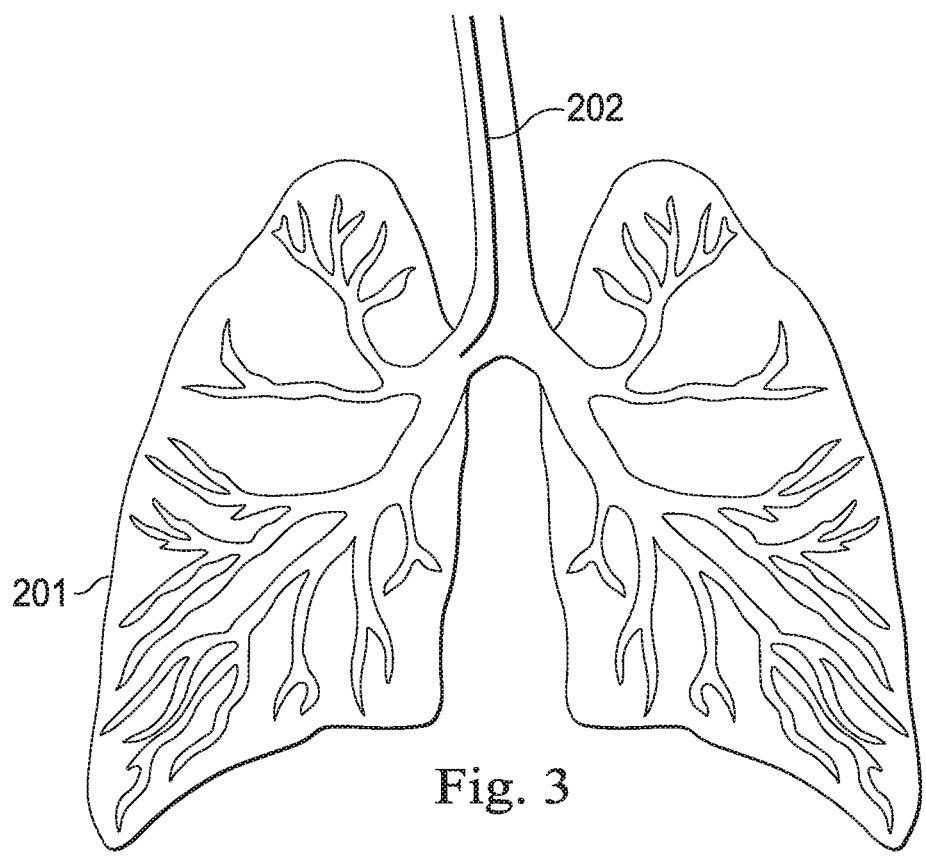
FIG. 3 illustrates the distal end of the medical instrument system of FIG. 2A positioned within a human lung.

FIG. 3 illustrates the catheter system 202 positioned within an anatomic passageway of a patient anatomy. In this embodiment, the anatomic passageway is an airway of human lungs 201. In alternative embodiments, the catheter system 202 may be used in other passageways of an anatomy.

Figure 4:
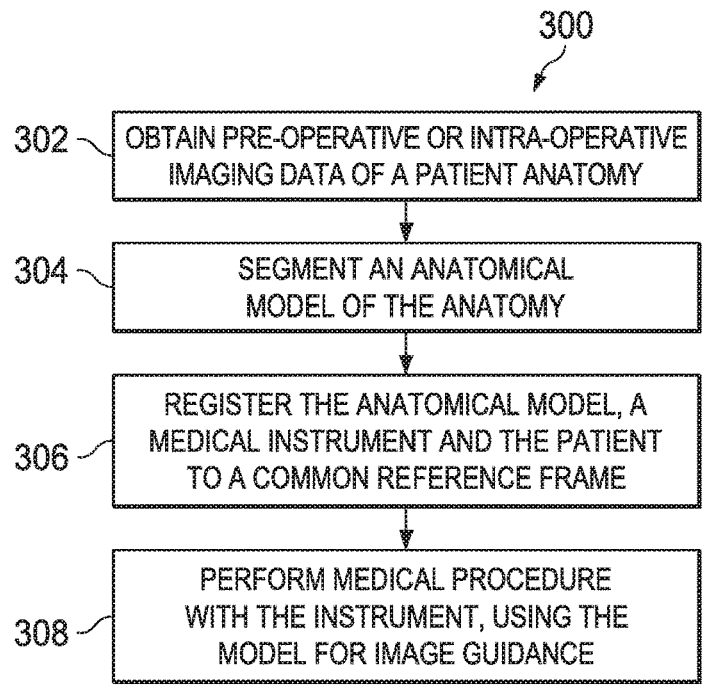
FIG. 4 is a flowchart illustrating a method used to provide guidance in an image-guided surgical procedure according to an embodiment of the present disclosure.

FIG. 4 is a flowchart illustrating a general method 300 for use in an image-guided surgical procedure. At a process 302, prior image data, including pre-operative or intra-operative image data, is obtained from imaging technology such as, computed tomography (CT), magnetic resonance imaging (MRI), thermography, ultrasound, optical coherence tomography (OCT), thermal imaging, impedance imaging, laser imaging, or nanotube X-ray imaging. The pre-operative or intra-operative image data may correspond to two-dimensional, three-dimensional, or four-dimensional (including e.g., time based or velocity based information) images. For example, the image data may represent the human lungs 201 of FIG. 3.

At a process 304, computer software alone or in combination with manual input is used to convert the recorded images into a segmented two-dimensional or three-dimensional composite representation or model of a partial or an entire anatomic organ or anatomic region. The composite representation and the image data set describe the various locations and shapes of the passageways and their connectivity. More specifically, during the segmentation process the images are partitioned into segments or elements (e.g., pixels or voxels) that share certain characteristics or computed properties such as color, density, intensity, and texture. This segmentation process results in a two- or three-dimensional reconstruction that forms a model of the target anatomy based on the obtained image. To represent the model, the segmentation process may delineate sets of voxels representing the target anatomy and then apply a function, such as marching cube function, to generate a 3D surface that encloses the voxels. The model may be made by generating a mesh, volume, or voxel map. Additionally or alternatively, the model may include a centerline model that includes a set of interconnected line segments or points extending through the centers of the modeled passageways. Where the model includes a centerline model including a set of interconnected line segments, those line segments may be converted to a cloud or set of points. By converting the line segments, a desired quantity of points corresponding to the interconnected line segments can be selected manually or automatically.

At a process 306, the anatomic model data, a medical instrument used to perform the medical procedure (e.g., instrument system 200), and the patient anatomy are co-registered in a common reference frame prior to and/or during the course of an image-guided surgical procedure on the patient. The common reference frame may be, for example, the surgical environment reference frame or the patient reference frame. The process 306 includes localizing the medical instrument with respect to the patient. The process 306 also includes registering the anatomic model with respect to the patient. Generally, registration involves the matching of measured point to points of the model through the use of rigid and/or non-rigid transforms. Measured points may be generated using landmarks in the anatomy, electromagnetic coils scanned and tracked during the procedure, or a shape sensor system. The measured points may be generated for use in an iterative closest point (ICP) technique. ICP and other registration techniques are described in U.S. Provisional Patent Application No. 62/205,440 and U.S. Provisional Patent Application No. 62/205,433, both filed Aug. 14, 2015, which are incorporated by reference herein in their entirety. At a process 308, the medical procedure may be performed using the anatomic model data to guide movement of the medical instrument.

Prior image data acquired, for example using CT, and used in an image guided surgical procedure often provides the fine anatomic detail suitable for many procedures. Prior image data, however, is subject to registration error and does not illustrate the real-time configuration of the anatomy, including any deformation due to cyclical or non-cyclical anatomic motion, the presence of and tissue deformation due to a medical instrument, or other alterations to the patient anatomy that may have occurred since the prior image data was obtained.

Traditional registration methods for use with image-guided surgery often involve the use of technologies based on electromagnetic or impedance sensing. In some instances, metallic objects or certain electronic devices used in the surgical environment may create disturbances that impair the quality of the sensed data. Additionally or alternatively, registration may be performed using perspective imaging systems such as fluoroscopic imaging systems and/or optical tracking systems. In some embodiments described herein, fluoroscopic imaging systems and/or optical tracking systems may be used to determine the location and orientation of medical instruments and patient anatomy within the coordinate system of the surgical environment. Although various provided examples describe the use of procedures performed within the anatomy, in alternative embodiments, the apparatus and methods of this disclosure need not be used within the anatomy but rather may also be used outside of the patient anatomy.

Fluoroscopy is an imaging modality that obtains real-time moving images of patient anatomy, medical instruments, and any radiopaque fiducial markers within the imaging field using X-rays. In this discussion, fiducial markers may also be referred to as fiducial elements or fiducials. A conventional radiograph is an X-ray image obtained by placing a part of the patient in front of an X-ray detector and then illuminating it with a short X-ray pulse. In a similar fashion, fluoroscopy uses X-rays to obtain real-time moving images of the interior of the patient, including radiopaque medical instruments, radiopaque dye, and/or radiopaque fiducial markers within the surgical environment. Fluoroscopic systems may include C-arm systems which provide positional flexibility and are capable of orbital, horizontal, and/or vertical movement via manual or automated control. Non-C-arm systems are stationary and provide less flexibility in movement. Fluoroscopy systems generally use either an image intensifier or a flat-panel detector to generate two dimensional real-time images of a patient anatomy. Bi-planar fluoroscopy systems simultaneously capture two fluoroscopic images, each from different (often orthogonal) viewpoints. The quality and utility of X-ray images may vary depending upon the type of tissue imaged. Denser material such as bone and metal are generally more visible in X-ray images than the air-filled soft tissue of the lung. For procedures in the lungs, prior-image CT data provides anatomical detail of airways and tumors that may be hard to discern on a fluoroscopy image, but the fluoroscopy image provide real-time visualization of the medical instruments and dense anatomical tissue.

An optical tracking system uses a position sensor to detect infrared-emitting or retro-reflective markers attached to the teleoperational assembly, the medical instrument, and/or patient. The position sensor calculates the position and orientation of the teleoperational assembly, the medical instrument, and/or patient based on the information the position sensor receives from those markers. More specifically, optical tracking systems use data captured from image sensors to triangulate the three dimensional position of the teleoperational assembly, the medical instrument, and/or patient between cameras calibrated to provide overlapping projections.

Thus, registered fluoroscopy, prior-image data, and/or optical tracking data may be used alone or in combination with kinematic data and shape sensor data to assist clinicians navigating certain portions of the anatomy, such as the lungs, by providing more accurate pose estimation and localization of the medical instruments. In particular, by obtaining fluoroscopic data of fiducial markers having known positions within the surgical coordinate system and/or shape properties, and combining the fluoroscopic data with either the positional or shape data of the fiducial markers, the teleoperational system can more accurately register the fluoroscopic imaging system to the surgical coordinate system, thereby increasing the reliability of instrument navigation during the surgical procedure.

Figure 5:
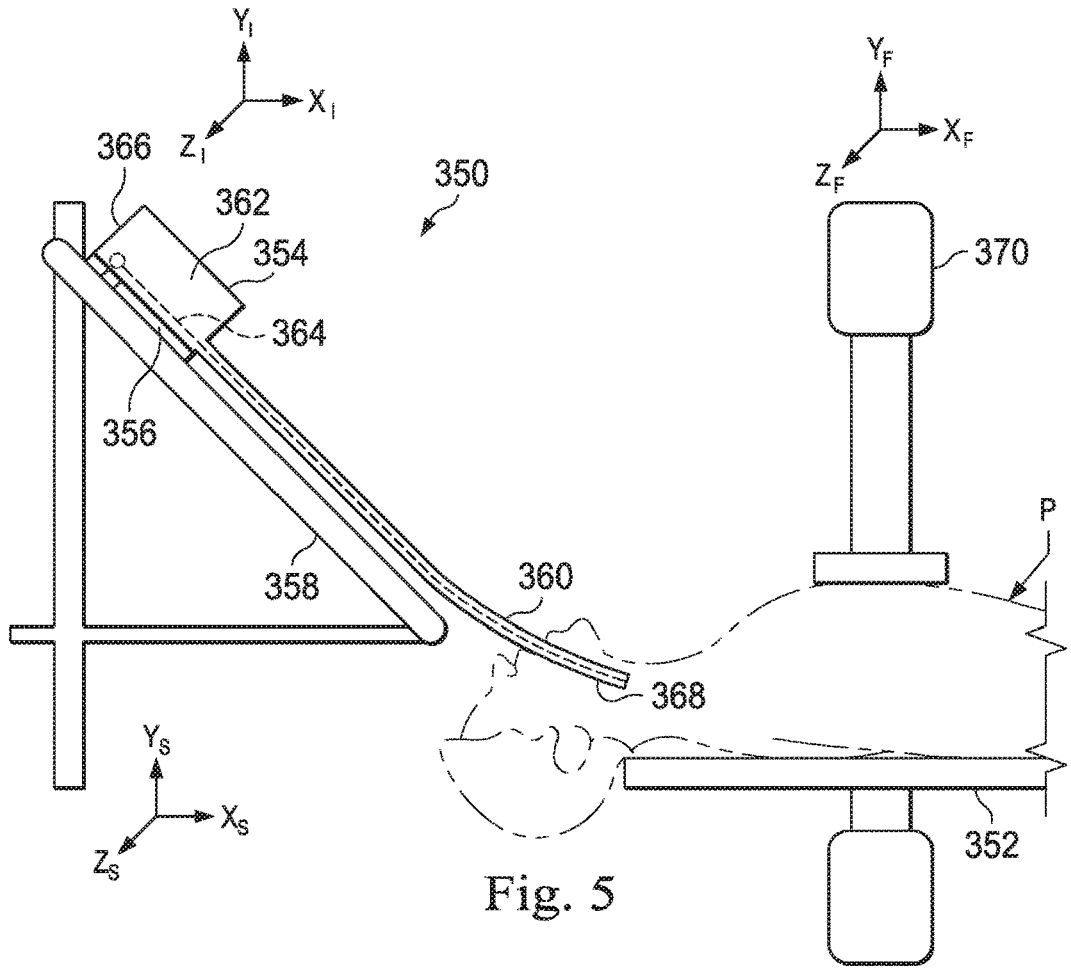
FIG. 5 is a side view of a patient coordinate space including a medical instrument mounted on an insertion assembly and an optical tracking system according to an embodiment of the present disclosure.

FIG. 5 illustrates an exemplary surgical environment 350 according to some embodiments, with a surgical coordinate system $X_S$, $Y_S$, $Z_S$, in which a patient P is positioned on a platform 352. The patient P may be stationary within the surgical environment in the sense that gross patient movement is limited by sedation, restraint, or other means. Cyclic anatomic motion including respiration and cardiac motion of the patient P may continue, unless the patient temporarily suspends respiratory motion. Within the surgical environment 350, a medical instrument 354 is coupled to an instrument carriage 356. The instrument carriage 356 is mounted to an insertion stage 358 fixed or movable within the surgical environment 350. The instrument carriage 356 may be a component of a teleoperational manipulator assembly (e.g., assembly 102) that couples to the instrument 354 to control insertion motion (i.e. motion in an $X_S$ direction) and, optionally, motion of a distal end of the instrument in multiple directions including yaw, pitch, and roll. The instrument carriage 356 or the insertion stage 358 may include servomotors (not shown) that control motion of the instrument carriage along the insertion stage.

The medical instrument 354 may include a flexible catheter 360 coupled to a proximal rigid instrument body 362.

The rigid instrument body 362 is coupled and fixed relative to the instrument carriage 356. An optical fiber shape sensor 364 extends along the instrument 354 and is operable to measure a shape from a fixed or known point 366 to another point such as a distal end portion 368 of the catheter 360. The medical instrument 354 may be substantially similar to the medical instrument system 200.

Figure 6A:
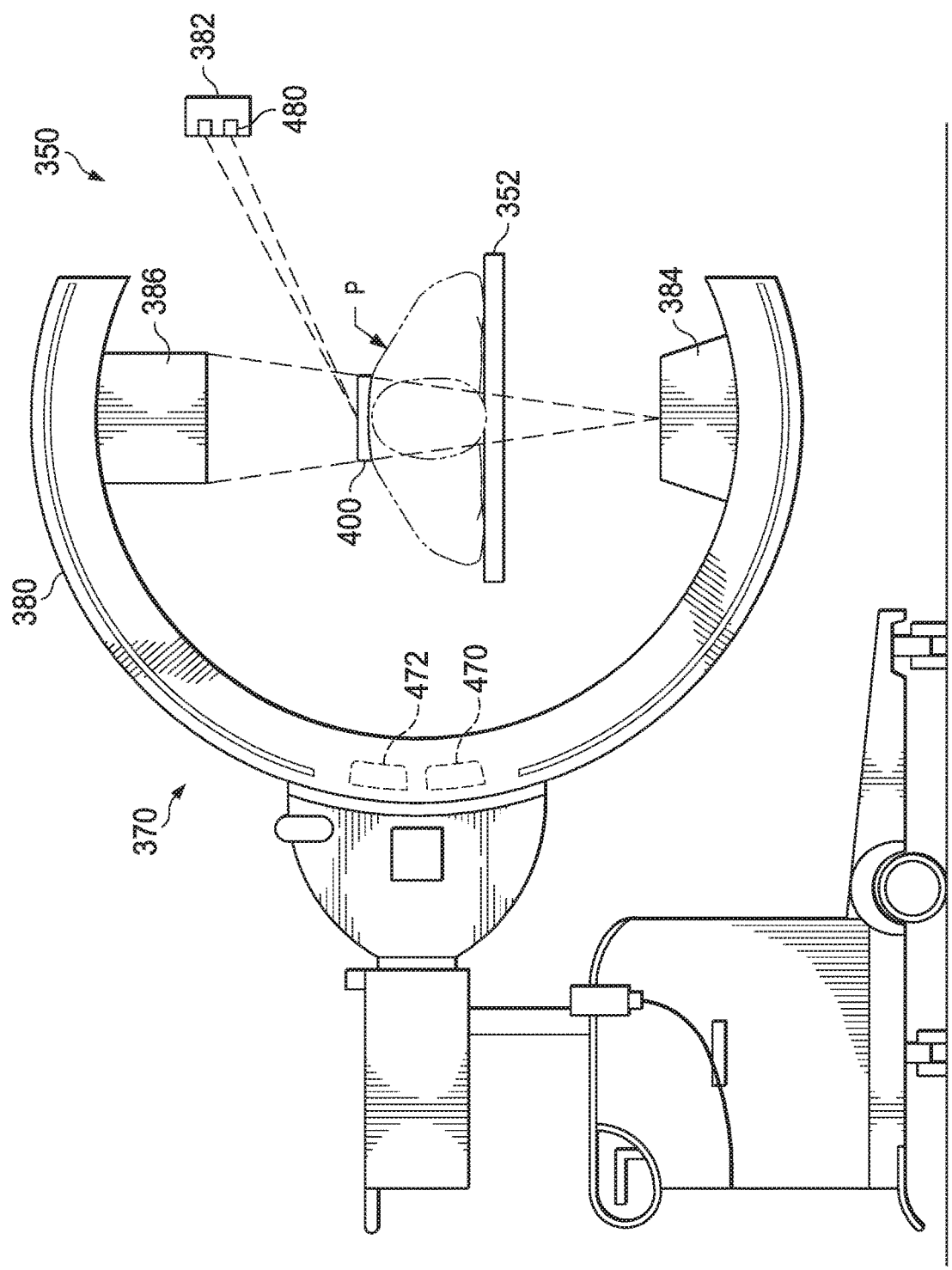
FIG. 6A is a different side view of the patient coordinate space shown in FIG. 5 including a C-arm of a fluoroscopic imaging system located in a first position relative to a patient and an external tracking system according to an embodiment of the present disclosure.
Figure 6B:
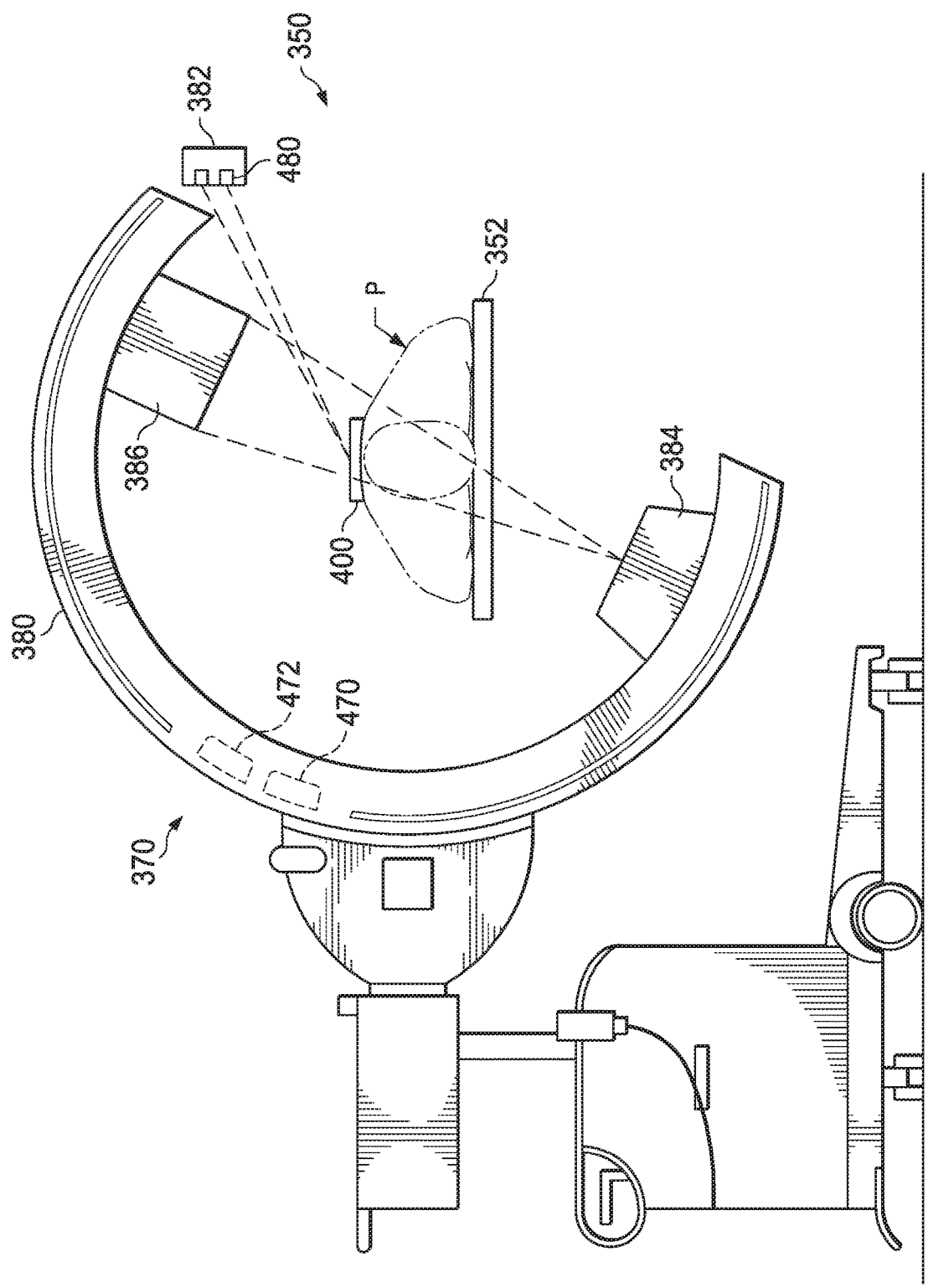
FIG. 6B is a side view of the patient coordinate space shown in FIG. 6A including the C-arm of the fluoroscopic imaging system located in a second position relative to the patient and the external tracking system according to an embodiment of the present disclosure.

A fluoroscopic imaging system 370 is arranged near the patient P to obtain fluoroscopic images of the patient while the catheter 360 is extended within the patient. The system 370 may be, for example as shown in FIGS. 6A and 6B, a mobile C-arm fluoroscopic imaging system. In some embodiments, the system 370 may be a multi-axis Artis Zeego fluoroscopic imaging system from Siemens Corporation of Washington, D.C.

FIGS. 6A and 6B illustrate another view of the exemplary surgical environment 350 shown in FIG. 5. FIG. 6A shows the fluoroscopic imaging system 370 including a mobile C-arm 380 that is located in a first position relative to the patient P and an external tracking system 382. In the pictured embodiment, the C-arm 380 includes an X-ray source 384 and an X-ray detector 386 (also "X-ray imager 386"). The X-ray detector 386 generates an image representing the intensities of received x-rays. Typically, the X-ray detector 386 comprises an image intensifier that converts the x-rays to visible light and a charge coupled device (CCD) video camera that converts the visible light to digital images. In operation, the patient P is positioned between the X-ray source 384 and the X-ray detector 386. In response to an operator's or teleoperational system's command input, X-rays emanating from the X-ray source 384 pass through patient P and into the X-ray detector 386, which generates a two-dimensional image of the patient.

Raw images generated by X-ray detector 386 tend to suffer from undesirable distortion (e.g., "barrel distortion" and/or "S-distortion") caused by a number of factors, including inherent image distortion in the image intensifier and external electromagnetic fields. Intrinsic calibration, which is the process of correcting image distortion in a received image and learning the projective geometry of the imager, involves placing fiducial markers 400 (also known as calibration markers) in the path of the X-ray, where a fiducial marker is an object opaque to X-rays. The fiducial markers 400 are rigidly arranged in predetermined patterns in one or more planes in the path of the X-rays and are visible in the recorded images. Because the true relative position of the fiducial markers 400 in the surgical environment is known (i.e., the undistorted position), the control system 112 is able to calculate an amount of distortion at each pixel in the resultant image (where a pixel is a single point in the image). Accordingly, the control system 112 can digitally compensate for the distortion in the original image and generate a distortion-free, or at least a distortion-improved digital image. Improving the accuracy of the true relative position of the fiducial markers 400 allows for enhanced pose estimation of the fluoroscopic imaging system 370, thereby increasing the accuracy of instrument pose determination and navigation during the surgical procedure.

Although each individual image taken by fluoroscopic imaging system 370 is a two-dimensional image, multiple two-dimensional images taken from different perspectives can be used to infer the three-dimensional location of an anatomical projection or medical instrument within the surgical field. To change image perspective, the C-arm 380 can be rotated as shown, for example, in FIG. 6B. The C-arm 380 can be pivoted to take X-ray images of the patient P and the fiducial marker 400 positioned within the field of view of the fluoroscopic imaging system 370 from different angles. FIG. 6B illustrates the surgical environment 350 shown in FIG. 6A with the C-arm 380 of the fluoroscopic imaging system 370 located in a second position relative to the patient P and the external tracking system 382. Three-dimensional tomographic images can be generated from the two-dimensional projection images created from different projection angles or viewpoints. By taking multiple two-dimensional images of the patient P and the fiducial marker 400 from different perspectives, the three-dimensional position of various points (e.g., various points on the fiducial marker 400) within the field of view may be determined.

As described above, the fiducial marker 400 comprises a radiopaque object, having a known configuration in the surgical environment, placed in the field of view of the fluoroscopic imaging system 370. The fiducial marker 400 appears in the fluoroscopic images for use as a point of reference or a measure. In the pictured embodiment, the fiducial marker 400 comprises a three dimensional object. In other embodiments, the fiducial marker may comprise a substantially one dimensional or two dimensional object. The fiducial markers 400 may be placed at fixed, predetermined positions in the x-ray imaging path to either obtain an image transformation that removes distortion from the original image generated by the X-ray detector 386 or to learn the projective geometry of the imager (i.e., to discern how a pixel in the image projects into three-dimensional space or to map the two-dimensional image of the fiducial marker to a known three-dimensional model). The fiducial markers 400 can be three-dimensional shapes that appear in the image as two-dimensional objects, but the fiducial markers 400 can also be constructed using thin films that are essentially two-dimensional in nature. Many possible shapes, such as, by way of non-limiting example, circles, squares, triangles, rectangles, ovals, cubes, spheres, and cylindrical rods, can be used to design the fiducial markers. Spheres appear in the two-dimensional image as circles and cylindrical rods appear as lines. Various types of fiducial marker design are described in U.S. Pat. App. No. 2010/0168562, entitled "Fiducial Marker Design and Detection for Locating Surgical Instrument in Images," filed Apr. 23, 2009, which is incorporated by reference herein in its entirety.

FIGS. 7A-9B illustrate a variety of exemplary fiducial markers. In some embodiments, as shown in FIG. 7A, the fiducial marker 400 may comprise a set of distinctive marker elements 401 such that each marker element 401a-f may be differentiated from another and the background features. In the pictured embodiment, each marker element 401a-f is a different shape. Additionally or alternatively, as shown in FIGS. 7B and 7C, the fiducial marker 400 may comprise a uniquely identifiable pattern of similar or dissimilar marker elements. For example, in FIG. 7B, the fiducial marker 402 comprises a grid pattern composed of identical fiducial elements 404, each of which is a white square surrounded by a dark border. Although each fiducial element may not be discernible from another, the grid layout of the fiducial marker 402 allows the marker to be uniquely identified within the surgical coordinate system. In contrast, in FIG. 7C, the fiducial marker 410 comprises a checkerboard grid pattern composed of two different fiducial elements: alternating dark squares 412 and light squares 414. Although each fiducial element may not be unique, the checkerboard layout of the fiducial marker 410 allows the marker to be uniquely identified and localized within the surgical coordinate system. In the grid and checkerboard patterns, each square has a fixed length and width in the surgical environment.

In some embodiments, the fiducial marker 400 may comprise a discernible marker that includes text and/or one or more symbols. FIG. 8A-8E illustrate some exemplary discernible fiducial markers, wherein each fiducial marker 422, 426, 432, 438, and 444 comprises a collection of distinct fiducial elements, and each fiducial element comprises a distinct alphabetical character. For example, the fiducial markers 422 and 444 are formed by a collection of distinct letters or fiducial elements (e.g., fiducial element 424 consists of the letter "E") that spell "Intuitive Surgical." Similarly, the fiducial marker 426 is formed by the fiducial elements 428 and 430, the fiducial marker 432 is formed by the fiducial elements 434 and 436, and the fiducial marker 438 is formed by the fiducial elements 440 and 442. The fiducial markers 434, 436, and 444 are each composed of distinct design patterns to allow for more detailed localization. The fiducial markers 422, 426, 432, 438, and 444 each employ variations of the checkerboard marker design described above with respect to the fiducial marker 410 shown in FIG. 7C. Although each fiducial element may not be unique, the overall shape and checkerboard layout of the fiducial markers 422, 426, 432, 438, and 444 allows it to be uniquely identified and localized within the surgical coordinate system.

In some embodiments, the fiducial marker 400 may comprise a series of similar fiducial elements arranged in a non-uniform linear pattern. For example, in FIGS. 9A and 9B, the fiducial markers 450 and 460 include a series of identical fiducial markers 452 and 462, respectively, arranged in a straight line with non-uniform spacing. In these embodiments, the non-uniform spacing of the fiducial markers 452, 462 forms uniquely identifiable codes upon imaging the fiducial markers 452 and 462, respectively. In some embodiments, such codes resemble a traditional (one-dimensional) or matrix (two-dimensional) barcode.

In the pictured embodiment, the fiducial marker 400 is shown positioned upon the patient P. In other embodiments, the fiducial marker 400 may be positioned above, aside, or under the patient P (e.g., on the platform 352). In one embodiment, for example, the checkerboard fiducial marker 410 shown in FIG. 7C may be positioned between the patient P and the platform 352. In yet other embodiments, the fiducial marker 400 may be found or positioned internally within the body of the patient P. For example, in some embodiments, the fiducial marker 400 may comprise the catheter 360 or the shape sensor 364 itself. In such embodiments, the catheter 360 and/or the shape sensor 364 are at least partially radiopaque. In some embodiments, the catheter 360 and/or the shape sensor 364 include one or more radiopaque fiducial elements as described above. In other embodiments, the catheter 360 and/or the shape sensor 364 are continuously radiopaque along at least their distal portions (e.g., the distal lengths that can be imaged by the fluoroscopic imaging system 370). Additionally or alternatively, the fiducial marker 400 may comprise an anatomical landmark of the patient P (e.g., one or more particular ribs). In other instances, the fiducial landmark 400 may be defined by radiopaque contrast ingested or injected into the patient P. Multiple identifiable locations on the fluoroscopic image along with the known length of the flexible device that contains the shape sensor can also serve as fiducial marker points. Additionally, images of the device in multiple shapes with a common grounding point can be combined to produce more fiducial marker points covering more space in three dimensions to reduce the ambiguity and/or to improve the accuracy of the calibration and/or the pose estimation. In a different embodiment, the entire device may be radiopaque, rather than specific identifiable locations on the device. The pose estimation can be performed by minimizing the back projection error of the three-dimensional curve of the shape of the device to an observed two-dimensional curve in the fluoroscopic image. In the same way, multiple images of multiple different shaped can be used to reduce the ambiguity and/or to improve the accuracy of the calibration and/or the pose estimation.

As mentioned above, obtaining multiple two-dimensional images of an object having known three-dimensional properties (e.g., the fiducial marker 400) from different perspectives allows for more accurate registration of the fluoroscopic imaging system 370 to the surgical coordinate space (i.e., by more precisely estimating the pose of the C-arm 380 and thus more accurately determining the perspective of the resultant two-dimensional images). The identification of the fiducial marker 400 in different imaging viewpoints and the intrinsic calibration of the fluoroscopic imaging system 370 may be done by using the cross-ratio as projective invariance. With reference to FIG. 10, the cross-ratio is a number associated with a list of four collinear points, particularly points on a projective line. Given four points A, B, C and D on a line, their cross ratio is defined as:

$$(A, B; C, D) = \frac{(AC \times BD)}{(BC \times AD)},$$

where an orientation of the line determines the sign of each distance and the distance is measured as projected into Euclidean space. FIG. 10 illustrates this cross-ratio principle, demonstrating that points A, B, C, D and A', B', C', D' are related by a projective transformation so that their cross-ratios, (A, B; C, D) and (A', B'; C', D') are equal.

FIGS. 11 and 12 illustrate two different methods of intrinsic calibration of the fluoroscopic imaging system 370 using the cross-ratio principle. In FIG. 11, the fluoroscopic imaging system 370 initially projects a two-dimensional fluoroscopic image (a planar projection) with the X-ray imager 386 at a first position P1, obtaining the positions of fiducial markers A and B at A' and B'. Subsequently, the fluoroscopic imaging system 370 projects another two-dimensional fluoroscopic image (a planar projection) with the X-ray imager 386 at a second position P2, obtaining the positions of fiducial markers A and B at A" and B". If the fiducial marker 400 is a planar calibration image, then the method depicted by FIG. 11, wherein the imager 386 examines the fiducial marker 400 from different angles, is particularly useful.

In FIG. 12, the X-ray imager 386 of the fluoroscopic imaging system 370 remains stationary and projects a first two-dimensional fluoroscopic image (a planar projection) with the fiducial markers A and B at a first position P3, obtaining the positions of fiducial markers A and B at A' and B'. Subsequently, the fluoroscopic imaging system 370 projects another two-dimensional fluoroscopic image (a planar projection) with the fiducial markers A and B positioned at a second position P4, obtaining the positions of fiducial markers A and B at A" and B". The four points A', B', A", and B" obtained in both scenarios may be used to intrinsically calibrate the fluoroscopic imaging system 370.

FIG. 13 is a flowchart illustrating a method 490 for performing image guided surgery in the surgical environment 350 that involves generally simultaneous localization/tracking of a medical instrument (e.g., the teleoperationally controlled instrument system 200) in the surgical environment and calibration of the fluoroscopic imaging system 370. The methods of this description, including method 490, are illustrated in FIG. 13 as a set of blocks, steps, operations, or processes. Not all of the illustrated, enumerated operations may be performed in all embodiments of the method 490. Additionally, some additional operations that are not expressly illustrated in the methods may be included before, after, in between, or as part of the enumerated processes. Some embodiments of the methods of this description include instructions that corresponded to the processes of the methods as stored in a memory. These instructions may be executed by a processor like a processor of the control system 112.

As described above, the pose of the fluoroscopic imaging system 370 (e.g., the position of the C-arm 380) within the surgical coordinate space is used to accurately determine the perspective of the two-dimensional fluoroscopic images. Accurately interpreting two-dimensional fluoroscopic images may also include recognizing and correcting image distortions. Process 500 describes an exemplary method of calibrating the fluoroscopic imaging system 370 to correct for distortions while simultaneously determining the pose of the fluoroscopic imaging system by imaging fiducial markers having known three-dimensional position, shape, and size characteristics in the surgical environment. The calibration process and the creation of a calibration model may be performed prior to the reconstruction of the instrument pose. The markers may be imaged by the fluoroscopic imaging system 370 from multiple different perspectives. At a process 502, the fluoroscopic imaging system 370 captures fluoroscopic image data of the fiducial marker 400, which has a known configuration (e.g. size, shape, location) in the surgical environment, from multiple perspectives or in multiple poses (as described above with respect to FIGS. 11 and 12). As will be described further below, the fiducial marker may include a shape sensor that provides shape and pose information for a flexible fiducial in the surgical environment.

At process 504, the control system 112 uses the fluoroscopic image data to estimate a set of intrinsic and extrinsic parameters of the fluoroscopic imaging system 370. For example, intrinsic parameters of the imaging system 370 include the calibration parameters of the imager such as focal length, the projection center, and the pixel scales. Extrinsic parameters of the imaging system 370 include location parameters of the imager such as rotation and translation and the rigid transformation between the fluoroscopic imaging system 370 and the calibration pattern or fiducial markers 400. At process 506, the control system 112 solves algorithms (e.g., using cross-ratios and projective invariance as shown in FIGS. 10-12) to create an estimated 3D model of the fluoroscopic imaging system 370 in relation to the surgical environment 350.

After iteratively imaging the fiducial marker 400 (and other fiducial markers if available) from different perspectives (e.g., by cycling through the processes 502, 504, and 506), the estimated model is refined, at a process 508, to a final model of the marker(s) in the surgical environment. The calibrated model is based on a set of optimal intrinsic and extrinsic parameters for the fluoroscopic imaging system 370 that correct for or at least minimize distortion, including S-distortion and provide an estimated pose for the imaging system in the surgical environment. The process 500 combines the two-dimensional location of fiducials in multiple fluoroscopic images together with known three-dimensional location estimates of the fiducials to reconstruct both intrinsic and extrinsic parameters. Methods of computer vision such as triangulation, bundle adjustment, or simultaneous localization and mapping (SLAM) might be used for reconstruction. At process 510, the calibrated model registers the fluoroscopic image reference frame to the surgical coordinate frame such that the pose of a marker imaged in the fluoroscopic reference frame can be determined in the surgical reference frame from the calibrated model. Registration of the fluoroscopic reference frame with the surgical reference frame and the anatomic model reference frame is described in incorporated by reference U.S. Provisional Pat. App. Nos. 62/205,440 and No. 62/205,433. Optionally, the calibration process 500 is supplemented with one or more various other processes. For example, a process 512 includes externally tracking the position and orientation of the fluoroscopic imaging system 370 to supplement the estimation of the pose of the imaging system 370 in the surgical environment. With reference to FIGS. 6A and 6B, the surgical environment 350 also includes the external tracker system 382. Generally, the external tracker system 382 comprises an external means to estimate the pose of the fluoroscopic imaging system 370 and/or the fiducial markers 400 with respect to the surgical coordinate system. Although the external tracker system 382 is depicted as spaced from the fluoroscopic imaging system 370, in some embodiments, the external tracker system 382 may be disposed on the fluoroscopic imaging system 370. For example, in various embodiments, the external tracker system 382 may comprise one or more encoders on the joints of the C-arm 380, as indicated by the dotted lines 470 of FIGS. 6A and 6B. Alternatively or additionally, the external tracker system 382 may comprise one or more inclinometers mounted on the C-arm 380 (e.g., one inclinometer per rotational degree-of-freedom of interest), as indicated by the dashed lines 472 of FIGS. 6A and 6B.

Alternatively or additionally, the external tracker system 382 may comprise an optical tracking system. In the pictured embodiment, the optical tracking system 382 includes a sensor 480 comprising a pair of cameras capable of emitting and receiving infrared rays reflected by at least one optical marker which include special reflectors positioned on reference arrays. In some embodiments, the sensor 480 may track the position of optical markers disposed on the C-arm 380. Additionally or alternatively, the sensor 480 may track the position of optical markers disposed on the patient P and/or the medical instrument (e.g., the catheter 360). In some embodiments, the fiducial marker 400 comprises an optical marker as well as a radiopaque marker. In some embodiments, the optical markers can be passive markers which include spherical, retro-reflective markers that reflect the infrared light emitted by illuminators on the sensor 480. In some embodiments, the fiducial markers may be active infrared-emitting markers that are activated by an electrical signal. Further descriptions of optical tracking systems are provided, for example, in U.S. Pat. No. 6,288,783, filed Oct. 28, 1999, disclosing, "System for determining spatial position and/or orientation of one or more objects," and U.S. Provisional Pat. App. No. 62/216,494, filed Sep. 10, 2015 disclosing "Systems And Methods For Using Optical Tracking In Image-Guided Surgery" which are incorporated by reference herein in their entirety. In some embodiments, as shown in FIG. 6A, the optical tracking sensor 480 tracks the set of optical fiducial markers attached to the fiducial marker 400 and/or the medical instrument as the instrument body moves the flexible catheter 360 into or out of the patient anatomy. In other embodiments, the external tracker system 382 may be used to estimate the pose of the fluoroscopic imaging system 370 independent of the intrinsic calibration process described above with respect to process 500 (reliant on the two-dimensional fluoroscopic images obtained of the fiducial markers 400).

After the fluoroscopic imaging system is calibrated and the markers are localized in the surgical environment, as described above, new fluoroscopic images can be registered to the surgical reference frame. At a process 514, during a medical procedure, a fluoroscopic image, in the fluoroscopic reference frame, is captured that includes the fiducial marker 400 and the catheter 360. At a process 516, from the fluoroscopic image, the position and orientation of one or more portions of the catheter (e.g., the distal tip portion) in the surgical reference frame is determined from the registration of the surgical reference frame to the fluoroscopic reference frame. More specifically, when a fluoroscopic image is received that includes the fiducial markers and the distal tip of the catheter in the same frame, the calibrated model, with the optional supplemental pose tracking of the fluoroscopic system, corrects for distortions and provides an estimated pose of the fluoroscopic imager. From the calibrated model, the pose of the distal tip of the catheter in the surgical reference frame may be determined.

As described above for FIG. 4, the method 300 for use in an image-guided surgical procedure includes localizing the medical instrument with respect to the patient in the surgical environment. Thus, some embodiments of the method 490 may include a process 492, in which prior image data, including pre-operative or intra-operative image data, is obtained from imaging technology such as, CT, MRI, thermography, ultrasound, OCT, thermal imaging, impedance imaging, laser imaging, or nanotube X-ray imaging. The prior image data may correspond to two-dimensional, three-dimensional, or four-dimensional (including e.g., time based or velocity based information) images. As described above, an anatomic model is created from the prior image data. At a process 494, the surgical reference frame ($X_S$, $Y_S$, $Z_S$) is registered to the instrument sensor reference frame ($X_I$, $Y_I$, $Z_I$). This registration between the model and instrument frames of reference may be achieved, for example, using a point-based ICP technique as described in incorporated by reference U.S. Provisional Pat. App. Nos. 62/205,440 and No. 62/205,433, which are incorporated by reference herein in their entirety. Additionally or alternatively, the model and sensor reference frames may be registered to another common reference frame. The common reference frame may be, for example, the surgical environment reference frame ($X_S$, $Y_S$, $Z_S$) or a patient reference frame. For example, a reference portion of the instrument sensor may be fixed, known, or tracked in the surgical environment.

At a process 518, the user or teleoperational system may perform the medical procedure with the medical instrument using the three-dimensional model and/or the fluoroscopic image data for guidance since both are registered to the surgical reference frame or another common reference frame. The processes 514-516 may be repeated throughout a medical procedure as the medical instrument is inserted or otherwise moved within the patient anatomy to provide current localization about the instrument relative to the anatomy and anatomical model.

Optionally, shape sensor data from shape sensor 364 may be used to complement the fluoroscopic data and intrinsic calibration process described by the process 500. The shape sensor data describes the shape of the sensor extending between the known reference point 366 on the rigid instrument body and the distal end of the flexible catheter 360. In some embodiments, as described above, the shape sensor 364 itself may act as the fiducial marker 400 because the shape sensor data provides the shape characteristics of the sensor (and the catheter through which it extends), including the pose of the distal tip, with known reference to the surgical frame of reference. Obtaining two-dimensional imaging data about a fiducial marker 400 such as the shape sensor 364 that has a known three-dimensional shape allows the control system 112 to more accurately localize the fiducial marker 400 within the surgical environment 350. When the shape sensor is used as a fiducial marker, it may be used as a lone fiducial marker or may be included in a plurality of one, two, and three dimensional fiducial markers present in the surgical environment. In some embodiments, the shape of the medical instrument or catheter 360 itself is at least partially radiopaque and acts as the fiducial marker 400. More specifically, the shape information combined with the location of the reference point 366 in the surgical environment, as tracked either kinematically and/or by the optical tracking sensor 480, provides the position and orientation of the distal tip of the flexible catheter 360 and other points along the catheter in the surgical environment. If the patient is also tracked by the optical tracking sensor 480, the position and orientation of the patient P is also known in the surgical environment. Thus, the position and orientation of the flexible catheter 360 is known with respect to the patient anatomy in the surgical environment frame of reference.

Fluoroscopic image data from multiple viewpoints (i.e., with the fluoroscopic imager moved among multiple locations) in the surgical environment may be compiled to generate two-dimensional or three-dimensional tomographic images. When using a fluoroscopic imager system that include a digital detector (e.g., a flat panel detector), the generated and compiled fluoroscopic image data permits the sectioning of planar images in parallel planes according to tomosynthesis imaging techniques. Traditional fluoroscopic imager movement has been limited to planar movement (e.g., a line or curve). For example, the fluoroscopic imager may be constrained to move linearly along a linear track or may be constrained to orbital movement defined by a C-arm. According to embodiments of this disclosure, two or three-dimensional movement of the fluoroscopic imager in the surgical environment generates fluoroscopic image data that provides greater detail about an area of interest in the patient anatomy as compared to image data generated by a fluoroscopic imager constrained to planar motion. With the pose of the fluoroscopic imager tracked according to any of the previously described methods, the fluoroscopic imager may be moved around in the three dimensional surgical space to capture image data that is tomographically combined to generate optimal images of a region of interest in the patient anatomy.

Due to constraints within a surgical environment (e.g., space, time, and cost) tomographic imaging techniques that use composite images from substantially less than the full range of the fluoroscopic imager may be used to prepare a tomographic image. For example, if a full scan range of motion of a C-arm fluoroscopic imager is approximately 200° for an automated scan, space limitations in the surgical environment due the presence of the teleoperational system may limit the imager from traveling the full 200°. However, useful tomographic images may be constructed by manually wobbling the imager in a constrained range (which defines a constrained scan region) substantially smaller than the 200° range. In one embodiment using a constrained range, the imager is wobbled or otherwise moved to one or more positions within an approximately 30° range, including positions both in the in-plane trajectory of the C-arm and optionally, out of the usual plane of the C-arm trajectory.

FIG. 14 illustrates a patient anatomy and a tomosynthesis arrangement 550 in a plane $X_S Y_S$ of a surgical environment. FIG. 15 illustrates the patient anatomy and tomosynthesis arrangement 550 of FIG. 14 in an orthogonal plane $Y_S Z_S$ of the surgical environment. An X-ray imager has a full scan range of motion R about the patient. As shown in FIG. 14, a patient P is imaged with the X-ray source moved within a constrained range to positions C1, C2, C3, C4, and C5 which is substantially smaller that the full scan range R. In this embodiment, the constrained range (in the $X_S Y_S$ plane) is approximately 300 or less than 20% of the full scan range. Patient P is imaged at a position C1 to an image plane I1. The X-ray source is rotated, wobbled, or otherwise manually moved in the $X_S Y_S$ plane (e.g., a first movement plane) to a position C2 to image the patient P to an image plane I2. The X-ray source is further rotated, wobbled, or otherwise manually moved in the $X_S Y_S$ plane to a position C3 to image the patient P to an image plane I3. The images I1, I2, I3 may be mapped and accumulated to a single tomographic plane T1 either by using the images themselves or after filtering by using a plan-projective transformation (i.e., homography) that is uniquely defined by the estimated poses of the X-ray source and the calibrated intrinsic parameters. The image reconstruction algorithms used to generate a slice image at the plane T1 blur or otherwise minimize features that are out of the plane T1. The tomographic plane T1 may be selected based upon the location of an anatomical region of interest or the location of a medical instrument. The same image data for the images I1, I2, I3 may also or alternatively be mapped to generate slice images in multiple tomographic planes such as plane T2 or plane T3. In this embodiment, the movement of the imager may be manually performed, but in other embodiments, the movement may be programmed or otherwise computer controlled. As shown more clearly in FIG. 15, the X-ray source may also be moved out of the $X_S Y_S$ plane into other movement planes within the constrained range. With the X-ray source moved to position C4, the patient is imaged to an image plane I4. With the X-ray source moved to position C5, the patient is imaged to an image plane I5. Any or all of the image data for the images I1, I2, I3, I4, I5 may be mapped to a single tomographic plane T4 or a single tomographic plane T5. The planes T4, T5 may be skew relative to each other and to the plane T1. In alternative embodiments, the X-ray imager at the positions C4 and C5 may be rotated to obtain multiple images across a range of angles for computing a tomosynthesis image. The images may be obtained at discrete locations, but, optionally, frames from a continuous fluoroscopic video can be used for reconstruction.

FIG. 16 illustrates a method 580 of image guided medical intervention using tomosynthesis image reconstruction from images obtained from multiple three-dimensional viewpoints of a fluoroscopic system in a surgical environment. As previously described, the pose and location of the fluoroscopic system in the surgical environment may be tracked using fluoroscopic markers in the fluoroscopic images and/or external trackers such as an optical tracking system or joint trackers (e.g., encoders) for the joints of the fluoroscopic system. Thus, the current or desired pose of the fluoroscopic imager in the surgical environment may be known or specified. The methods of this description, including method 580, are illustrated in FIG. 16 as a set of blocks, steps, operations, or processes. Not all of the illustrated, enumerated operations may be performed in all embodiments of the method 580. Additionally, some additional operations that are not expressly illustrated in the methods may be included before, after, in between, or as part of the enumerated processes. Some embodiments of the methods of this description include instructions that corresponded to the processes of the methods as stored in a memory. These instructions may be executed by a processor like a processor of the control system 112.

At a process 582, fluoroscopic image data of a patient anatomy is received from a fluoroscopic imager (e.g., imaging system 370) positioned at locations C1, C2, C3 within the surgical coordinate space. At a process 584, the tomographic image T1 is constructed from the fluoroscopic image data. The image may be displayed to a clinician in real-time during a medical procedure on the patient P. If the image lacks sufficient detail of an area of interest, additional tomosynthetic planar images may be useful. The clinician may, for example, identify a region of interest (e.g., a region in which a tumor is located) by selecting a region of the image using an operator input device such as a touch screen, a mouse, or a trackball. Alternatively, a region of interest for generating further planar tomosynthetic images may be selected by identifying a region of interest in a pre-operative CT registered to the surgical environment. Alternatively, a region of interest for generating further planar tomosynthetic images may be selected by determining the location of a portion of the medical instrument, such as the distal tip, in the registered surgical environment and the trajectory of an instrument (e.g., a biopsy needle) extending therefrom.

At a process 586, based on the identified region of interest, instructions may be generated for moving the fluoroscopic imager to another pose, set of poses, or range of imaging angles in the three-dimensional surgical coordinate space. After or during movement, the pose of the fluoroscopic imager, may be tracked, as previously described, using fluoroscopic markers in the fluoroscopic images and/or external trackers such as an optical tracking system or joint trackers (e.g., encoders) for the joints of the fluoroscopic system. The fluoroscopic imager is not limited to movement in a single plane. Rather, the movement of the fluoroscopic imager is unconstrained, allowing the imager to be posed in configurations that provide optimal imaging data. The instructions may be control signals that instruct a control system of the fluoroscopic imager to move the fluoroscopic imager to a specified pose in the surgical coordinate system. Alternatively, the instructions may be displayed or otherwise communicated to an operator to manually move the fluoroscopic imager to a specified pose in the surgical coordinate system. The fluoroscopic imager may be freely movable about the surgical coordinate system and not constrained to linear or orbital motion in a single plane. Alternatively, the moving instructions may include instructions for relocating the imaging system 370 and obtaining multiple fluoroscopic images in a single plane from the relocated position. For example, the C-arm may be moved to a new location based upon the instructions, and the C-arm may be rotated to generate a plurality of images from the plane of rotation.

At a process 588, additional fluoroscopic image data of a patient anatomy may be received from the fluoroscopic imager positioned at the specified pose or set of poses within the surgical coordinate space. For example, the region of interest may be in the plane T4, so the imager may be moved to position C4 to generate additional fluoroscopic image data. At a process 590, a second planar tomographic image may be constructed from the second fluoroscopic image data. The second fluoroscopic image data may generated from a single image or from a plurality of images. In various embodiments, the second planar tomographic image may be constructed from the second fluoroscopic image data combined with the first fluoroscopic image data. The reconstruction of desired structures may be achieved by repeated and continuous processing with new images added and accumulated. Thus, process steps similar to 586, 588, 590 may be repeated until the resulting tomosynthetic image includes the desired structures, such as the tumor, the catheter, or the pleural boundary. The pose history of the fluoroscopic imager may be tracked and provided to a user via a display or other user interface so that the user knows which poses and/or ranges of angles in the surgical environment have been covered.

Although the systems and methods of this disclosure have been described for use in the connected bronchial passageways of the lung, they are also suited for navigation and treatment of other tissues, via natural or surgically created connected passageways, in any of a variety of anatomical systems including the colon, the intestines, the kidneys, the brain, the heart, the circulatory system, or the like.

Also, although this disclosure describes various systems and methods for teleoperated systems, they are also contemplated for use in non-teleoperated systems where manipulator assemblies and instruments are directly controlled. Although various provided examples describe the use of procedures performed within the anatomy, in alternative embodiments, the apparatus and methods of this disclosure need not be used within the anatomy but rather may also be used outside of the patient anatomy.

One or more elements in embodiments of the invention may be implemented in software to execute on a processor of a computer system such as control system 112. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

The invention claimed is:

1. A method performed by a computing system, the method comprising:

receiving, from a fluoroscopic imager, first intraoperative fluoroscopic image data of a fiducial marker within a surgical coordinate space;

receiving a configuration of the fiducial marker within the surgical coordinate space;

based on the configuration of the fiducial marker, calculating an amount of distortion at each pixel in the first intraoperative fluoroscopic image data of the fiducial marker;

determining a set of calibration parameters of the fluoroscopic imager in the surgical coordinate space based on the first intraoperative fluoroscopic image data and the configuration of the fiducial marker, wherein determining the set of calibration parameters comprises developing a calibrated model of the fiducial marker in the surgical coordinate space from the first intraoperative fluoroscopic image data and the configuration of the fiducial marker;

correcting the amount of distortion in the first intraoperative fluoroscopic image data using the calibrated model;

registering, based on the calibrated model of the fiducial marker, a fluoroscopic imager reference frame to a surgical coordinate reference frame of the surgical coordinate space; and determining a pose of the fiducial marker in the surgical coordinate reference frame based on the registration.

2. The method of claim 1, further comprising:

localizing the fiducial marker in the surgical coordinate space based on the configuration of the fiducial marker that comprises a set of fiducial marker elements forming a uniquely identifiable pattern.

3. The method of claim 1, wherein developing the calibrated model includes determining intrinsic parameters and extrinsic parameters for the fluoroscopic imager.

4. The method of claim 1, further comprising:

receiving, from the fluoroscopic imager, second intraoperative fluoroscopic image data of the fiducial marker and a portion of a medical instrument; and localizing the portion of the medical instrument in the surgical coordinate space, based on the set of calibration parameters of the fluoroscopic imager, relative to the surgical coordinate space.

5. The method of claim 1, further comprising:

receiving shape information from a shape sensor included in the fiducial marker to determine the configuration of the fiducial marker within the surgical coordinate space.

6. The method of claim 5, wherein the shape sensor is a fiber optic sensor.

7. The method of claim 5, wherein the fiducial marker is included in a flexible catheter in which the shape sensor is extended.

8. The method of claim 7, wherein receiving the shape information includes receiving different shapes of the flexible catheter.

9. The method of claim 1, wherein the first intraoperative fluoroscopic image data includes images of a plurality of fiducial markers, the plurality of fiducial markers including the fiducial marker, the plurality of fiducial markers having a known configuration within the surgical coordinate space.

10. The method of claim 1, wherein the fiducial marker is included in a medical instrument, the medical instrument including an elongated flexible body.

11. The method of claim 1, wherein determining the set of calibration parameters of the fluoroscopic imager includes receiving external tracking data for the fluoroscopic imager.

12. The method of claim 11, wherein the fluoroscopic imager comprises a mobile C-arm, and wherein the external tracking data is received from an encoder positioned on the mobile C-arm or is received from an inclinometer positioned on the mobile C-arm.

13. The method of claim 11, wherein the external tracking data is received from an optical tracking sensor configured to track positions of optical fiducials positioned on the fluoroscopic imager.

14. A computer-assisted medical system comprising:
one or more processors; and
a fiducial marker positioned in a known configuration within a surgical coordinate space, the fiducial marker including a shape sensor, wherein the one or more processors are configured to perform a method including:
receiving, from a fluoroscopic imager, first intraoperative fluoroscopic image data of the fiducial marker;
receiving shape information from the shape sensor;
deriving the known configuration of the fiducial marker within the surgical coordinate space from the shape information;
based on the known configuration of the fiducial marker, calculating an amount of distortion at each pixel in the first intraoperative fluoroscopic image data of the fiducial marker;
developing a calibrated model of the fiducial marker in the surgical coordinate space from the first intraoperative fluoroscopic image data and the known configuration of the fiducial marker derived from the shape information;
determining a set of calibration parameters of the fluoroscopic imager in the surgical coordinate space based on the calibrated model;
correcting the amount of distortion in the first intraoperative fluoroscopic image data using the calibrated model; and
determining a pose of the fiducial marker in the surgical coordinate space based on the set of calibration parameters of the fluoroscopic imager.

15. The system of claim 14, wherein developing a calibrated model includes determining intrinsic parameters and extrinsic parameters for the fluoroscopic imager.

16. The system of claim 14, wherein the method performed by the one or more processors further includes:
receiving, from the fluoroscopic imager, second intraoperative fluoroscopic image data of the fiducial marker and a portion of a medical instrument; and
localizing the portion of the medical instrument in the surgical coordinate space based on the set of calibration parameters of the fluoroscopic imager relative to the surgical coordinate space.

17. The system of claim 14, wherein the first intraoperative fluoroscopic image data includes images of a plurality of fiducial markers, the plurality of fiducial markers including the fiducial marker, the plurality of fiducial markers having a known configuration within the surgical coordinate space.

18. The system of claim 14, wherein the fiducial marker is included in a medical instrument, the medical instrument including an elongated flexible body.

19. The system of claim 14, further comprising:
localizing the fiducial marker in the surgical coordinate space based on the known configuration of the fiducial marker.

20. The system of claim 19, wherein the fiducial marker includes a set of fiducial marker elements.

21. The system of claim 20, wherein each one in the set of fiducial marker elements is differentiated from one another.

22. A method performed by a computing system, the method comprising:
receiving, from a fluoroscopic imager, first intraoperative fluoroscopic image data of a fiducial marker within a surgical coordinate space;
receiving a configuration of the fiducial marker within the surgical coordinate space;
determining a set of parameters of the fluoroscopic imager in the surgical coordinate space based on the first intraoperative fluoroscopic image data and the configuration of the fiducial marker, wherein determining the set of parameters comprises developing a calibrated model of the fiducial marker in the surgical coordinate space from the first intraoperative fluoroscopic image data and the configuration of the fiducial marker, wherein the set of parameters includes at least one of a focal length, a projection center, pixel scales, rotation of the fluoroscopic imager, or translation of the fluoroscopic imager;
registering, based on the calibrated model of the fiducial marker, a fluoroscopic imager reference frame to a surgical coordinate reference frame of the surgical coordinate space; and
determining a pose of the fiducial marker in the surgical coordinate reference frame based on the registration.

23. The method of claim 22, wherein the first intraoperative fluoroscopic image data includes images of a plurality of fiducial markers, the plurality of fiducial markers including the fiducial marker, the plurality of fiducial markers having a known configuration within the surgical coordinate space.

24. The method of claim 22, further comprising:
receiving shape information from a shape sensor included in the fiducial marker to determine the configuration of the fiducial marker within the surgical coordinate space.

25. The method of claim 24, wherein the fiducial marker is included in a flexible catheter in which the shape sensor is extended, and wherein receiving the shape information includes receiving different shapes of the flexible catheter.

* * * * *